United States Patent
Burghes et al.

(10) Patent No.: US 10,357,543 B2
(45) Date of Patent: Jul. 23, 2019

(54) METHODS AND COMPOSITIONS FOR TREATING DISORDERS AND DISEASES USING SURVIVAL MOTOR NEURON (SMN) PROTEIN

(71) Applicants: OHIO STATE INNOVATION FOUNDATION, Columbus, OH (US); THE RESEARCH INSTITUTE AT NATIONWIDE CHILDREN'S HOSPITAL, Columbus, OH (US)

(72) Inventors: Arthur Burghes, Columbus, OH (US); William Arnold, Pickerington, OH (US); Brian Kaspar, New Albany, OH (US); Vicki McGovern, Hilliard, OH (US)

(73) Assignees: Ohio State Innovation Foundation, Columbus, OH (US); The Research Institute At Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 15/775,675

(22) PCT Filed: Nov. 16, 2016

(86) PCT No.: PCT/US2016/062225
§ 371 (c)(1),
(2) Date: May 11, 2018

(87) PCT Pub. No.: WO2017/087486
PCT Pub. Date: May 26, 2017

(65) Prior Publication Data
US 2018/0353572 A1     Dec. 13, 2018

Related U.S. Application Data

(60) Provisional application No. 62/255,721, filed on Nov. 16, 2015.

(51) Int. Cl.
| | |
|---|---|
| *A61K 38/16* | (2006.01) |
| *A61K 38/17* | (2006.01) |
| *A61K 31/519* | (2006.01) |
| *A61K 31/7105* | (2006.01) |
| *A61K 31/711* | (2006.01) |
| *A61K 31/7115* | (2006.01) |
| *A61K 31/712* | (2006.01) |
| *A61K 31/713* | (2006.01) |
| *C12N 15/113* | (2010.01) |
| *A61P 21/00* | (2006.01) |
| *A61K 38/18* | (2006.01) |

(52) U.S. Cl.
CPC ............ *A61K 38/18* (2013.01); *A61K 31/519* (2013.01); *A61K 31/711* (2013.01); *A61K 31/712* (2013.01); *A61K 31/7105* (2013.01); *A61K 31/7115* (2013.01); *A61K 38/1709* (2013.01); *A61P 21/00* (2018.01); *C12N 15/113* (2013.01)

(58) Field of Classification Search
None
See application file for complete search history.

(56) References Cited

U.S. PATENT DOCUMENTS

| | | | |
|---|---|---|---|
| 5,783,565 | A  | 7/1998  | Lee et al. |
| 5,837,533 | A  | 11/1998 | Boutin |
| 5,981,505 | A  | 11/1999 | Weiner et al. |
| 6,127,170 | A  | 10/2000 | Boutin |
| 6,217,900 | B1 | 4/2001  | Ciccarelli et al. |
| 6,376,508 | B1 | 4/2002  | Li et al. |
| 6,379,965 | B1 | 4/2002  | Boutin |
| 6,383,512 | B1 | 5/2002  | Ciccarelli et al. |
| 6,693,187 | B1 | 2/2004  | Dellinger |
| 6,747,014 | B2 | 6/2004  | Teng et al. |
| 6,838,283 | B2 | 1/2005  | Bennett et al. |
| 7,067,641 | B2 | 6/2006  | Dellinger |
| 7,202,227 | B2 | 4/2007  | Boutin |
| 7,691,847 | B2 | 4/2010  | Dreyfuss et al. |
| 8,586,559 | B2 | 11/2013 | Singh et al. |
| 2004/0192746 | A1 | 9/2004 | Sanner et al. |
| 2006/0286167 | A1 | 12/2006 | Staunton et al. |
| 2009/0042900 | A1 | 2/2009 | Singh et al. |
| 2010/0136678 | A1 | 6/2010 | Li |
| 2010/0267812 | A1 | 10/2010 | Dodge et al. |
| 2012/0149756 | A1 | 6/2012 | Schuemperli et al. |
| 2013/0096160 | A1 | 4/2013 | Marugan et al. |
| 2013/0344135 | A1 | 12/2013 | van Rooij et al. |
| 2014/0193906 | A1 | 7/2014 | Androphy et al. |
| 2014/0206661 | A1 | 7/2014 | Axford et al. |

(Continued)

FOREIGN PATENT DOCUMENTS

| | | |
|---|---|---|
| EP | 0711833    | 5/1996 |
| EP | 0999270    | 5/2000 |
| WO | 2001066129 | 9/2001 |

(Continued)

OTHER PUBLICATIONS

Aagaard P, Suetta C, Caserotti P, Magnusson SP, Kjaer M. Role of the nervous system in sarcopenia and muscle atrophy with aging: strength training as a countermeasure. Scandinavian journal of medicine & science in sports. Feb. 2010;20(1):49-64.

(Continued)

*Primary Examiner* — Tracy Vivlemore
(74) *Attorney, Agent, or Firm* — Meunier Carlin & Curfman LLC

(57) ABSTRACT

Disclosed are methods and compositions related to treatment and prevention of sarcopenia and/or nerve injury by increasing survival motor neuron (SMN) levels in an individual in need thereof.

26 Claims, 7 Drawing Sheets

(56) References Cited

U.S. PATENT DOCUMENTS

| | | |
|---|---|---|
| 2014/0329772 A1 | 11/2014 | Linsley et al. |
| 2015/0275205 A1 | 10/2015 | Miller et al. |

FOREIGN PATENT DOCUMENTS

| | | |
|---|---|---|
| WO | 03/093449 | 11/2003 |
| WO | 2005072720 | 8/2005 |
| WO | 2009042907 | 4/2009 |
| WO | 2009120700 | 10/2009 |
| WO | 2009146033 | 12/2009 |
| WO | 2010120820 | 10/2010 |
| WO | 2010148249 | 12/2010 |
| WO | 2011130515 | 10/2011 |
| WO | 2012160130 | 11/2012 |
| WO | 2012175714 | 12/2012 |
| WO | 2013112788 | 8/2013 |
| WO | 2013173638 | 11/2013 |
| WO | 2013181391 | 12/2013 |
| WO | 2014012050 | 1/2014 |
| WO | 2014102778 | 7/2014 |
| WO | 2015017589 | 2/2015 |

OTHER PUBLICATIONS

Andreassi C, et al., Aclarubicin treatment restores SMN levels to cells derived from type I spinal muscular atrophy patients. Human Molecular Genetics, 2001, 2841-2849.

Arnold WD, Burghes AH. Spinal muscular atrophy: The development and implementation of potential treatments. Annals of neurology, 2013, 20 pages.

Arnold WD, Kassar D, Kissel JT. Spinal muscular atrophy: Diagnosis and management in a new therapeutic era. Muscle Nerve, 2015, 157-167.

Arnold WD, Porensky PN, McGovern VL, et al. Electrophysiological Biomarkers in Spinal Muscular Atrophy: Preclinical Proof of Concept. Annals of clinical and translational neurology. Jan. 1, 2014;1(1):34-44.

Atkins JL, Whincup PH, Morris RW, Lennon LT, Papacosta O, Wannamethee SG. Sarcopenic obesity and risk of cardiovascular disease and mortality: a population-based cohort study of older men. Journal of the American Geriatrics Society. Feb. 2014;62(2):253-260.

Avila MA, Trichostatin A increases SMN expression and survival in a mouse model of spinal muscular atrophy. The Journal of Clinical Investigation http://www.jci.org vol. 117 No. 3, 659-671.

Batsis JA, Mackenzie TA, Bane LK, Lopez-Jimenez F, Bartels SJ. Sarcopenia, sarcopenic obesity and mortality in older adults: results from the National Health and Nutrition Examination Survey III. European journal of clinical nutrition. Sep. 2014;68(9):1001-1007.

Bauder AR, Ferguson TA. Reproducible mouse sciatic nerve crush and subsequent assessment of regeneration by whole mount muscle analysis. Journal of visualized experiments: JoVE. 2012(60), 7 pages.

Baughan, et al., Stimulating Full-Length SMN2 Expression by Delivering Bifunctional RNAs via a Viral Vector. Molecular Therapy vol. 14, No. 1, Jul. 2006, 9 pages.

Bevan AK, Duque S, Foust KD, et al. Systemic gene delivery in large species for targeting spinal cord, brain, and peripheral tissues for pediatric disorders. Molecular therapy: the journal of the American Society of Gene Therapy. Nov. 2011;19(11):1971-1980.

Bevan AK, Hutchinson KR, Foust KD, et al. Early heart failure in the SMNDelta7 model of spinal muscular atrophy and correction by postnatal scAAV9-SMN delivery. Hum Mol Genet. Oct. 15, 2010;19(20):3895-3905.

Biondi O, Grondard C, Lecolle S, et al. Exercise-induced activation of NMDA receptor promotes motor unit development and survival in a type 2 spinal muscular atrophy model mouse. J Neurosci. Jan. 23, 2008;28(4):953-962.

Branchu, et al., Shift from Extracellular Signal-Regulated Kinase to AKT/cAMP Response Element-Binding Protein Pathway Increases Survival-Motor-Neuron Expression in Spinal-Muscular-Atrophy-Like Mice and Patient Cells, The Journal of Neuroscience, Mar. 6, 2013 • 33(10):4280-4294.

Burghes AH, Beattie CE. Spinal muscular atrophy: why do low levels of survival motor neuron protein make motor neurons sick? Nature Reviews Neuroscience. 2009;10(8):597-609.

Burnett BG, Munoz E, Tandon A, Kwon DY, Sumner CJ, Fischbeck KH. Regulation of SMN protein stability. Molecular and cellular biology. Mar. 2009;29(5):1107-1115.

Burns, et al., Development of a Protein-Based Therapy for the Treatment of Spinal Muscular Atroph. Department of Biochemistry, Microbiology, & Immunology Faculty of Medicine University of Ottawa 2014, 112 pages.

Campbell MJ, McComas AJ, Petito F. Physiological changes in ageing muscles. Journal of Neurology, Neurosurgery & Psychiatry. Apr. 1, 1973 1973;36(2):174-182.

Carlson BM. The regeneration of skeletal muscle. A review. The American journal of anatomy. Jun. 1973;137(2):119-149.

Chai RJ, Vukovic J, Dunlop S, Grounds MD, Shavlakadze T. Striking denervation of neuromuscular junctions without lumbar motoneuron loss in geriatric mouse muscle. PloS one. 2011;6(12):e28090.

Cherry, et al., Assays for the Identification and Prioritization of Drug Candidates for Spinal Muscular Atrophy. ASSAY and Drug Delivery Technol. 12(6), 2014, 315-341.

Cherry, et al., Enhancement of SMN protein levels in a mouse model of spinal muscular atrophy using novel drug-like compounds. EMBO Mol Med (2013) 5, 1035-1050.

Delbono O. Neural control of aging skeletal muscle. Aging cell. Feb. 2003;2(1):21-29.

Delmonico MJ, Harris TB, Visser M, et al. Longitudinal study of muscle strength, quality, and adipose tissue infiltration. Am J Clin Nutr. Dec. 2009;90(6):1579-1585.

Dickson, et al., A Negatively Acting Bifunctional RNA Increases Survival Motor Neuron Both In Vitro and In Vivo. Human Gene Therapy 2008, 19:1307-1315.

DiDonato, et al., Development of a Gene Therapy Strategy for the Restoration of Survival Motor Neuron Protein Expression: Implications for Spinal Muscular Atrophy Therapy. Human Gene Therapy 2003, 179-188.

Doherty TJ, Vandervoort AA, Brown WF. Effects of ageing on the motor unit: a brief review. Canadian journal of applied physiology = Revue canadienne de physiologie appliquee. Dec. 1993;18(4):331-358.

Duque SI, Arnold WD, Odermatt P, et al. A large animal model of Spinal Muscular Atrophy and correction of phenotype. Annals of neurology, 2015, 77(3), 399-414.

Fahim MA. Morphological correlates of physiological responses in partially denervated mouse muscle during aging. International Journal of Developmental Neuroscience. 6// 1993;11(3):303-310.

Farooq, et al., Prolactin increases SMN expression and survival in a mouse model of severe spinal muscular atrophy via the STAT5 pathway. The Journal of Clinical Investigation, 121(8), 2011, 3042-3050.

Faulkner JA, Larkin LM, Claflin DR, Brooks SV. Age-related changes in the structure and function of skeletal muscles. Clinical and experimental pharmacology & physiology. Nov. 2007;34(11):1091-1096.

Foust KD, Wang X, McGovern VL, et al. Rescue of the spinal muscular atrophy phenotype in a mouse model by early postnatal delivery of SMN. Nat Biotech. 2010;28(3):271-274.

Fu AKY, Cheung ZH, Ip NY. [beta]-catenin in reverse action. Nat Neurosci. 03//print 2008;11(3):244-246.

Garbes, et al., LBH589 induces up to 10-fold SMN protein levels by several independent mechanisms and is effective even in cells from SMA patients non-responsive to valproate. Human Molecular Genetics, 2009, vol. 18, No. 19 3645-3658.

Gennarelli M, Lucarelli M, Capon F, et al. Survival motor neuron gene transcript analysis in muscles from spinal muscular atrophy patients. Biochem Biophys Res Commun. Aug. 4, 1995;213(1):342-348.

(56) References Cited

OTHER PUBLICATIONS

Gogliotti, et al., The DcpS inhibitor RG3039 improves survival, function and motor unit pathologies in two SMA mouse models. Human Molecular Genetics, 2013, vol. 22, No. 20 4084-4101.

Gooch CL, Mosier DR. Stimulated single fiber electromyography in the mouse: techniques and normative data. Muscle Nerve. Jul. 2001;24(7):941-945.

Goodpaster BH, Park SW, Harris TB, et al. The loss of skeletal muscle strength, mass, and quality in older adults: The Health, Aging and Body Composition Study. J Gerentol Med Sci. 2006;61: 1059-1064.

Harahap, et al., Valproic acid increases SMN2 expression and modulates SF2/ASF and hnRNPA1 expression in SMA fibroblast cell lines. Brain & Development 34 (2012) 213-222.

Hastings, et al., Tetracyclines That Promote SMN2 Exon 7 Splicing as Therapeutics for Spinal Muscular Atrophy. Sci Transl Med. Nov. 4, 2009; 1(5): 5ra12.

Hauke, et al., Survival motor neuron gene 2 silencing by DNA methylation correlates with spinal muscular atrophy disease severity and can be bypassed by histone deacetylase inhibition. Human Molecular Genetics, 2009, vol. 18, No. 2 304-317.

Howell, et al., Advances in therapeutic development for spinal muscular atrophy., Future Med Chem. Jun. 2014; 6(9): 1081-1099.

Hsieh-Li HM, Chang J-G, Jong Y-J, et al. A mouse model for spinal muscular atrophy. Nat Genet. 2000;24(1):66-70.

Hsu, et al., Triptolide increases transcript and protein levels of survival motor neurons in human SMA fibroblasts and improves survival in SMA-like mice. British Journal of Pharmacology (2012) 166 1114-1126.

Ikeda K, Wong V, Holmlund TH, et al. Histometric effects of ciliary neurotrophic factor in wobbler mouse motor neuron disease. Annals of neurology. Jan. 1995;37(1):47-54.

Jacob JM, Robbins N. Age differences in morphology of reinnervation of partially denervated mouse muscle. J Neurosci. May 1990;10(5):1530-1540.

Jang YC, Lustgarten MS, Liu Y, et al. Increased superoxide in vivo accelerates age-associated muscle atrophy through mitochondrial dysfunction and neuromuscular junction degeneration. FASEB journal: official publication of the Federation of American Societies for Experimental Biology. May 2010;24(5):1376-1390.

Jarecki, et al., Diverse small-molecule modulators of SMN expression found by high-throughput compound screening: early leads towards a therapeutic for spinal muscular atrophy. Human Molecular Genetics, 2005, vol. 14, No. 14 2003-2018.

Juel VC. Evaluation of neuromuscular junction disorders in the electromyography laboratory. Neurologic clinics. May 2012;30(2):621-639.

Kablar B, Belliveau AC. Presence of neurotrophic factors in skeletal muscle correlates with survival of spinal cord motor neurons. Developmental dynamics: an official publication of the American Association of Anatomists. Nov. 2005;234(3):659-669.

Kallman DA, Plato CC, Tobin JD. The role of muscle loss in the age-related decline of grip strength: cross-sectional and longitudinal perspectives. Journal of gerontology. May 1990;45(3):M82-88.

Kariya S, Obis T, Garone C, et al. Requirement of enhanced Survival Motoneuron protein imposed during neuromuscular junction maturation. The Journal of clinical investigation. Feb. 3, 2014;124(2):785-800.

Kariya S, Park GH, Maeno-Hikichi Y, et al. Reduced SMN protein impairs maturation of the neuromuscular junctions in mouse models of spinal muscular atrophy. Hum Mol Genet. Aug. 15, 2008;17(16):2552-2569.

Kawamura Y, O'Brien P, Okazaki H, Dyck PJ. Lumbar motoneurons of man II: the number and diameter distribution of large- and intermediate-diameter cytons in "motoneuron columns" of spinal cord of man. Journal of neuropathology and experimental neurology. Sep.-Oct. 1977;36(5):861-870.

Kennis E, Verschueren S, Van Roie E, Thomis M, Lefevre J, Delecluse C. Longitudinal impact of aging on muscle quality in middle-aged men. Age (Dordrecht, Netherlands). 2014;36(4):9689.

Kolb, et al., Initial Testing (Stage 1) of AZD6244 (ARRY-142886) by the Pediatric Preclinical Testing Program. Pediatr Blood Cancer. Oct. 2010, 55(4): 668-677.

Koliatsos VE, Clatterbuck RE, Winslow JW, Cayouette MH, Prices DL. Evidence that brain-derived neurotrophic factor is a trophic factor for motor neurons in vivo. Neuron. 3// 1993;10(3):359-367.

Landi F, Cruz-Jentoft AJ, Liperoti R, et al. Sarcopenia and mortality risk in frail older persons aged 80 years and older: results from ilSIRENTE study. Age Ageing. Mar. 2013;42(2):203-209.

Landis SC, Amara SG, Asadullah K, et al. A call for transparent reporting to optimize the predictive value of preclinical research. Nature. 10/11/print 2012;490(7419):187-191.

Larsson L, Ansved T. Effects of ageing on the motor unit. Progress in neurobiology. Apr. 1995;45(5):397-458.

Lefebvre S, Burglen L, Reboullet S, et al. Identification and characterization of a spinal muscular atrophy-determining gene. Cell. Jan. 13, 1995;80(1):155-165.

Lewelt, et al., New Therapeutic Approaches to Spinal Muscular Atrophy. Curr Neurol Neurosci Rep (2012) 12:42-53.

Li J GT, Arnold WD, Rosen GD, Zaworski PG, Rutkove SB. A comparison of three electrophysiological methods for the assessment of disease status in a mild spinal muscular atrophy mouse model. PloS one. 2014, e111428.

Li Y, Lee Yi, Thompson WJ. Changes in Aging Mouse Neuromuscular Junctions Are Explained by Degeneration and Regeneration of Muscle Fiber Segments at the Synapse. The Journal of Neuroscience. Oct. 19, 2011 2011;31(42):14910-14919.

Ling KKY, Gibbs RM, Feng Z, Ko C-P. Severe neuromuscular denervation of clinically relevant muscles in a mouse model of spinal muscular atrophy. Human Molecular Genetics. Jan. 1, 2012 2012;21(1):185-195.

Lorson CL, Androphy EJ. An exonic enhancer is required for inclusion of an essential exon in the SMA-determining gene SMN. Hum Mol Genet. Jan. 22, 2000;9(2):259-265.

Lorson CL, Strasswimmer J, Yao JM, et al. SMN oligomerization defect correlates with spinal muscular atrophy severity. Nat Genet. May 1998;19(1):63-66.

Lorson, et al., SMN-inducing compounds for the treatment of spinal muscularAtrophy. Future Med Chem. Oct. 2012; 4(16): 2067-2084.

Makhortova, et al., A Screen for Regulators of Survival of Motor Neuron Protein Levels. Nat Chem Biol.; 7(8): 544-552.

Manini TM, Visser M, Won-Park S, et al. Knee extension strength cutpoints for maintaining mobility. Journal of the American Geriatrics Society. Mar. 2007;55(3):451-457.

Martinez, et al., Survival Motor Neuron Protein in Motor Neurons Determines Synaptic Integrity in Spinal Muscular Atrophy. The Journal of Neuroscience, Jun. 20, 2012, 32(25):8703-8715.

McAndrew PE, Parsons DW, Simard LR, et al. Identification of proximal spinal muscular atrophy carriers and patients by analysis of SMNT and SMNC gene copy number. American journal of human genetics. Jun. 1997;60(6):1411-1422.

Meekins GD, Carter GT, Emery MJ, Weiss MD. Axonal degeneration in the Trembler-j mouse demonstrated by stimulated single-fiber electromyography. Muscle Nerve. Jul. 2007;36(1):81-86.

Melton LJ, 3rd, Khosla S, Crowson CS, O'Connor MK, O'Fallon WM, Riggs BL. Epidemiology of sarcopenia. Journal of the American Geriatrics Society. Jun. 2000;48(6):625-630.

Misic MM, Rosengren KS, Woods JA, Evans EM. Muscle quality, aerobic fitness and fat mass predict lower-extremity physical function in community-dwelling older adults. Gerontology. 2007;53(5):260-266.

Mittal KR, Logmani FH. Age-related reduction in 8th cervical ventral nerve root myelinated fiber diameters and numbers in man. Journal of gerontology. Jan. 1987;42(1):8-10.

Mohan R, Tosolini AP, Morris R. Targeting the motor end plates in the mouse hindlimb gives access to a greater number of spinal cord motor neurons: An approach to maximize retrograde transport. Neuroscience. Aug. 22, 2014;274(0):318-330.

Mohseni, et al., Histone deacetylase inhibitors as potential treatment for spinal muscular atrophy. Genetics and Molecular Biology, 36, 3, 299-307.

(56) References Cited

OTHER PUBLICATIONS

Monani UR, Sendtner M, Coovert DD, et al. The human centromeric survival motor neuron gene (SMN2) rescues embryonic lethality in Smn−/− mice and results in a mouse with spinal muscular atrophy. Human Molecular Genetics. Feb. 12, 2000 2000;9(3):333-339.

Muscaritoli et al. (2010), Consensus definition of sarcopenia, cachexia and pre-cachexia: joint document elaborated by Special Interest Groups (SIG) "cachexia-anorexia in chronic wasting diseases" and "nutrition in geriatrics". Clinical Nutrition 29(2):154-9.

Naryshkin NA, Weetall M, Dakka A, et al. SMN2 splicing modifiers improve motor function and longevity in mice with spinal muscular atrophy. Science (New York, N.Y.). Aug. 8, 2014 2014;345(6197):688-693.

Newman AB, Haggerty CL, Goodpaster B, et al. Strength and muscle quality in a well-functioning cohort of older adults: The Health, Aging and Body Composition Study. Journal of the American Geriatrics Society. Mar. 2003;51(3):323-330.

Newman AB, Kupelian V, Visser M, et al. Strength, but not muscle mass, is associated with mortality in the health, aging and body composition study cohort. The journals of gerontology. Series A, Biological sciences and medical sciences. Jan. 2006;61(1):72-77.

Oda K. Age changes of motor innervation and acetylcholine receptor distribution on human skeletal muscle fibers. Journal of the neurological sciences. Nov.-Dec. 1984;66(2-3):327-338.

Pane, et al., Daily salbutamol in young patients with SMA type II. Neuromuscular Disorders 18 (2008) 536-540.

Passini, et al., CNS-targeted gene therapy improves survival and motor function in a mouse model of spinal muscular atrophy. The Journal of Clinical Investigation 2010, 1253-1264.

Passini, et al., Translational Fidelity of Intrathecal Delivery of Self-Complementary AAV9-Survival Motor Neuron 1 for Spinal Muscular Atrophy. Human Gene Therapy 2014, 25:619-630.

Riessland, et al., SAHA ameliorates the SMA phenotype in two mouse models for spinal muscular atrophy. Human Molecular Genetics, 2010, vol. 19, No. 8 1492-1506.

Riessland, et al., The benzamide M344, a novel histone deacetylase inhibitor, significantly increases SMN2 RNA/protein levels in spinal muscular atrophy cells. Hum Genet (2006) 120:101-110.

Rigaud M, Gemes G, Barabas ME, et al. Species and strain differences in rodent sciatic nerve anatomy: implications for studies of neuropathic pain. Pain. May 2008;136(1-2):188-201.

Ruggiu M, McGovern VL, Lotti F, et al. A role for SMN exon 7 splicing in the selective vulnerability of motor neurons in spinal muscular atrophy. Molecular & Cellular Biology. 2012;32(1):126-138.

Sayer AA, Robinson SM, Patel HP, Shavlakadze T, Cooper C, Grounds MD. New horizons in the pathogenesis, diagnosis and management of sarcopenia. Age and Ageing. Mar. 1, 2013 2013;42(2):145-150.

Schlesinger and Dubensky (1999), Alphavirus vectors for gene expression and vaccines. Curr. Opin. Biotechnol. 5:434-439.

Shavlakadze T, McGeachie J, Grounds MD. Delayed but excellent myogenic stem cell response of regenerating geriatric skeletal muscles in mice. Biogerontology. Jun. 2010;11(3):363-376.

Stalberg E, Trontelj JV. The study of normal and abnormal neuromuscular transmission with single fibre electromyography. Journal of neuroscience methods. Jun. 27, 1997;74(2):145-154.

Sugarman EA, Nagan N, Zhu H, et al. Pan-ethnic carrier screening and prenatal diagnosis for spinal muscular atrophy: clinical laboratory analysis of >72,400 specimens. European journal of human genetics: EJHG. Jan. 2012;20(1):27-32.

Summer, et al., Therapeutics Development for Spinal Muscular Atrophy. The Journal of the American Society for Experimental NeuroTherapeutics, 2006, 253-245.

Tanaka K, Webster HD. Myelinated fiber regeneration after crush injury is retarded in sciatic nerves of aging mice. The Journal of comparative neurology. Jun. 8, 1991;308(2):180-187.

Tiziano, et al., Salbutamol increases survival motor neuron (SMN) transcript levels in leucocytes of spinal muscular atrophy (SMA) patients: relevance for clinical trial design. J Med Genet 2010;47: 856e858.

Tomlinson BE, Irving D. The numbers of limb motor neurons in the human lumbosacral cord throughout life. Journal of the neurological sciences. Nov. 1977;34(2):213-219.

Valdez G, Tapia JC, Kang H, et al. Attenuation of age-related changes in mouse neuromuscular synapses by caloric restriction and exercise. Proceedings of the National Academy of Sciences of the United States of America. Aug. 17, 2010;107(33):14863-14868.

Van Meerbeke, et al., The DcpS inhibitor RG3039 improves motor function in SMA mice. Human Molecular Genetics, 2013, vol. 22, No. 20 4074-4083.

Van Mier P, Lichtman J. Regenerating muscle fibers induce directional sprouting from nearby nerve terminals: studies in living mice. The Journal of Neuroscience. Sep. 1, 1994 1994;14(9):5672-5686.

Verdu E, Buti M, Navarro X. The effect of aging on efferent nerve fibers regeneration in mice. Brain Res. Oct. 23, 1995;696(1-2):76-82.

Wang Z-M, Zheng Z, Messi ML, Delbono O. Extension and magnitude of denervation in skeletal muscle from ageing mice. The Journal of physiology. 2005;565(3):757-764.

Wirth, et al., Spinal muscular atrophy: state-of-the-art and therapeutic perspectives. ALS and other motor neuron disorders 2002 3, 87-95.

Xiao, et al., Discovery, Synthesis and Biological Evaluation of Novel SMN Protein Modulators. J Med Chem. Sep. 22, 2011; 54(18): 6215-6233.

Ying et al. (1999), Cancer therapy using a self-replicating RNA vaccine. Nat. Med. 5(7):823-827.

Yuan Q, Su H, Guo J, et al. Decreased c-Jun expression correlates with impaired spinal motoneuron regeneration in aged mice following sciatic nerve crush. Experimental gerontology. Apr. 2012;47(4):329-336.

Yuan R, Tsaih S-W, Petkova SB, et al. Aging in inbred strains of mice: study design and interim report on median lifespans and circulating IGF1 levels. Aging Cell. 2009;8(3):277-287.

Yuo, et al., 5-(N-ethyl-N-isopropyl)-amiloride Enhances SMN2 Exon 7 Inclusion and Protein Expression in Spinal Muscular Atrophy Cells. American Neurology Association 2007, 26-34.

International Preliminary Report on Patentability issued for Application No. PCT/US2016/062225, dated May 31, 2018.

International Searching Authority (U.S.). International Search Report and Written Opinion. Application No. PCT/US2016/062225, dated Jan. 24, 2017. 11 pages.

METHODS AND COMPOSITIONS FOR TREATING DISORDERS AND DISEASES USING SURVIVAL MOTOR NEURON (SMN) PROTEIN

CROSS-REFERENCE TO RELATED APPLICATIONS

This application claims benefit of U.S. Provisional Application No. 62/255,721, filed Nov. 16, 2015, incorporated herein by reference in its entirety.

BACKGROUND

Aging-related muscle wasting and weakness (sarcopenia) is an important problem of an increasingly aging society (Faulkner et al. 2007; Manini et al. 2007). Though sarcopenia is a multifactorial phenomenon, a number of studies have indicated the presence of marked denervated and atrophied muscle fibers (Chai et al. 2011; Valdez et al. 2010; Tomlinson et al. 1977; Oda et al. 1984; Kawamura et al. 1977). Indeed, using electromyographic techniques that allow longitudinal monitoring of motor unit function in the mouse in vivo (Arnold et al. 2014), a reduction in the number of functional motor neurons innervating the hind limb muscles have been identified as an early feature in aging mice. The motor unit is comprised of a single motor neuron and the muscle fibers it innervates. Motor unit synaptic connectivity is maintained by trophic support from various compartments (Fu et al. 2008; Koliatsos et al. 1993; Ikeda et al. 1995; Kablar et al. 2005), and it is suggested that the maintenance of motor neuron connectivity and repair of neuromuscular junctions (NMJs) is critical in aging.

Peripheral nerves are commonly injured from trauma including automobile accidents, motorcycle accidents, surgeries, knife and projectile wounds and birth injuries to both the child and mother. Common surgical causes of nerve injury include prostatectomy and mastectomy. Other common injuries during surgery are the result of long-term limb positioning or inevitable or accidental nerve compression. Following nerve injury there is a loss of sensation and/or function in the regions of the body innervated by the damaged nerve. For example, following nerve injury from prostatectomy there is commonly erectile dysfunction. Following mastectomy there is often loss of proper function of the upper extremity and/or scapula. Furthermore, following birth injury or other trauma with damage to the brachial plexus there is dysfunction in the ipsilateral limb. What is needed are methods and compositions related to treating sarcopenia and nerve injury in a subject in need thereof.

SUMMARY

Disclosed herein is a method of reducing sarcopenia in an individual, the method comprising: identifying an individual with sarcopenia, an individual with symptoms of sarcopenia, or an individual at risk for developing sarcopenia, wherein the subject is 35 years old or older; and administering to the individual a Survival Motor Neuron (SMN) protein-increasing substance, thereby reducing sarcopenia, sarcopenia symptoms, or the risk of sarcopenia in the individual.

Also disclosed is a method of treating an individual with nerve damage, the method comprising: identifying a subject with nerve damage; and administering to the subject a Survival Motor Neuron (SMN) protein-increasing substance, thereby reducing nerve damage and/or improving nerve function in the individual.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The accompanying figures, which are incorporated in and constitute a part of this specification, illustrate several aspects described below.

FIG. 2A shows images of motor neuron samples both pre-LCM and post-LCM. FIG. 2B shows mRNA levels of motor neuron and non-motor neuron samples.

DETAILED DESCRIPTION

Definitions

Figure 1A:
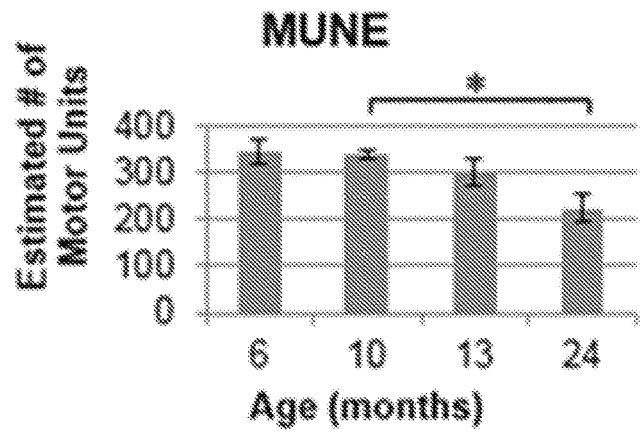
FIGS. 1A-1D show electromyographic data in cohorts of male C57BL/6J mice at different ages. Overview of electromyographic findings in C57BL/6J male mice at 6 (n=10), 10 (n=10), 13 (n=10), and 24 months (n=6) of age is shown. For MUNE, CMAP, and SMUP, comparison between 10 m and 24 month old mice was performed. Single fiber EMG was performed in two cohorts of animals at 6 and 14 month old animals. A. MUNE (number of total functional motor units) is diminished in 24 month old mice (224±36; p=0.027) compared with 10 month old mice (341±29; p=0.027). B. When compared with CMAP response in 10 month old mice (50.7 mV±3.9), a reduction in 24 month old mice (38.2 mV±3.8; p=0.034) is noted. C. Similarly, an increase in the single motor unit potential (SMUP) amplitude is seen in 24 month old mice (360 µV±38) but this is not statistically significant (p=0.144) compared with 10 month old mice (282 µV±23). D. Alteration in NMJ transmission (increased jitter) are noted in 14 month old (jitter=14.7±1.1 µs, n=22 individual synapses, obtained from 2 mice) versus 6 month old mice (jitter=10.8±1.4 µs, n=18 individual synapses, obtained from 2 mice) (p=0.043) (Data shown as mean±standard error of the mean) (ns, not significant; *, p<0.05).
Figure 1B:
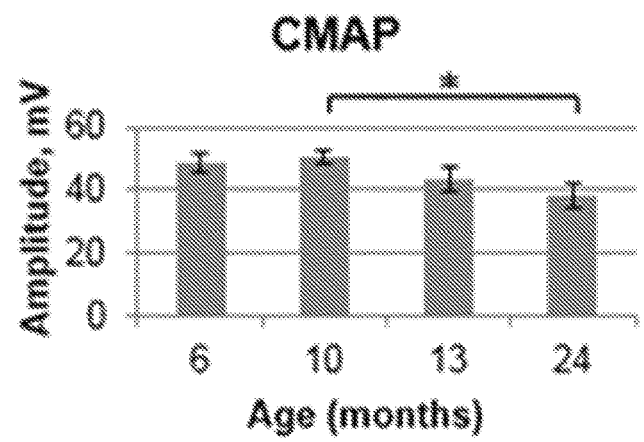

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of .+−0.20% or .+−. 10%, more preferably .+−0.5%, even more preferably .+−. 1%, and still more preferably .+−0.0.1% from the specified value, as such variations are appropriate to perform the disclosed methods.

A "prophylactic" treatment is a treatment administered to a subject who does not exhibit signs of a disease or exhibits only early signs for the purpose of decreasing the risk of developing pathology. The compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

By "Survival Motor Neuron (SMN)-increasing substance" is meant any substance that increases the amount of SMN in an individual. Examples include, but are not limited to, compounds, compositions, antisense oligonucleotides, long non coding RNAs or treatment therapies. "SMN-increasing substance" includes diverse classes of substances that can be used to increase SMN levels. Determining which compounds are able to increase SMN levels can be accomplished by those of skill in the art. Examples of such substances are described herein.

An "analogue," "analog" or "derivative," which are used interchangeably, refers to a compound, e.g., a peptide or polypeptide, substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" a disease means to reduce the frequency or severity of at least one sign or symptom of a disease or disorder.

An "effective amount" as used herein, means an amount which provides a therapeutic or prophylactic benefit.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

As used herein, the term "cell" is herein used in its broadest sense in the art, referring to a structural unit of a tissue present in a multicellular organism, which is capable of self-replicating, has genetic information and a mechanism for expressing it, and is surrounded by a membrane structure that isolates the living body from the outside. Cells used herein may be either naturally-occurring cells or artificially modified cells (e.g., fusion cells, genetically modified cells, etc.), as long as the cell has a chemical receptor or is capable of having such a nucleic acid molecule introduced therein. Examples of cell sources include, but are not limited to, a single-cell culture; the embryo, blood, or a body tissue of a normally-grown transgenic animal, a mixture of cells derived from normally-grown cell lines, and the like. In some preferred embodiments, a cell which is easily transformed or transfected is used.

As used herein, the term "tissue" refers to an aggregate of cells having substantially the same function and/or form in a multi-cellular organism. "Tissue" is typically an aggregate of cells of the same origin, but may be an aggregate of cells of different origins as long as the cells have the same function and/or form. Typically, a tissue constitutes a part of an organ. Animal tissues are separated into epithelial tissue, connective tissue, muscular tissue, nervous tissue, and the like, on a morphological, functional, or developmental basis.

As used herein, the term "isolated" means that naturally accompanying material is at least reduced, or preferably substantially completely eliminated, in normal circumstances. Therefore, the term "isolated cell" refers to a cell substantially free from other accompanying substances (e.g., other cells, proteins, nucleic acids, etc.) in natural circumstances. The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are subsequently chemically synthesized.

As used herein, the term "gene" refers to an element defining a genetic trait. A gene is typically arranged in a given sequence on a chromosome. A gene which defines the primary structure of a protein is called a structural gene. A gene which regulates the expression of a structural gene is called a regulatory gene (e.g., promoter). As used herein, "gene" may refer to a "polynucleotide", "oligonucleotide", "nucleic acid", and a "nucleic acid molecule."

As used herein, "gene product" includes a "polynucleotide", "oligonucleotide", a "nucleic acid" and a "nucleic acid molecule" and/or "protein", "polypeptide", "oligopeptide" and a "peptide", which are subsequent expression products of a gene. Those skilled in the art understand what a gene product is, according to the context used with embodiments of the present invention. Accordingly, gene used herein usually includes not only double-stranded DNA but also each single-stranded DNA, such as sense strand and antisense strand constituting thereof. Therefore, in embodiments of the present invention, the genes can include any of double-stranded DNA including human genome DNA, and single-stranded DNA (sense strand) including cDNA, as well as a single stranded DNA (antisense) having a sequence complementary to the sense strand, as well as fragments thereof.

The terms "polynucleotide", "oligonucleotide", "nucleic acid molecule" and "nucleic acid" as used herein have the same meaning and refer to a nucleotide polymer having any length. This term also includes an "oligonucleotide derivative" or a "polynucleotide derivative". An "oligonucleotide derivative" or a "polynucleotide derivative" includes a nucleotide derivative, or refers to an oligonucleotide or a polynucleotide having linkages between nucleotides different from typical linkages, which are interchangeably used.

As used herein, the term "fragment" with respect to a polypeptide or polynucleotide refers to a polypeptide or polynucleotide having a sequence length ranging from 1 to n−1 with respect to the full length of the reference polypeptide or polynucleotide (of length n). The length of the fragment can be appropriately changed depending on the purpose. For example, in the case of polypeptides, the lower limit of the length of the fragment includes 3, 4, 5, 6, 7, 8, 9, 10, 15, 20, 25, 30, 40, 50 or more nucleotides. Lengths represented by integers which are not herein specified (e.g., 1 1 and the like) can be appropriate as a lower limit. For example, in the case of polynucleotides, the lower limit of the length of the fragment includes 5, 6, 7, 8, 9, 10, 15, 20, 25, 30, 40, 50, 75, 100 or more nucleotides. Lengths represented by integers which are not herein specified (e.g., 1 1 and the like) may be appropriate as a lower limit. As used herein, the length of polypeptides or polynucleotides can be represented by the number of amino acids or nucleic acids, respectively. However, the above-described numbers are not absolute. The above-described numbers, as the upper or lower limits, are intended to include some greater or smaller numbers (e.g., .±10%), as long as the same function is maintained. In embodiments of the present invention, it is understood that any fragment can be used as long as the fragment functions as possessing transposition activity.

A "control" is an alternative subject or sample used in an experiment for comparison purpose. A control can be "positive" or "negative". For example, where the purpose of the experiment is to determine a correlation of an altered expression level of a gene with a particular type of pathology, it is generally preferable to use a positive control (a subject or a sample from a subject, carrying such alteration and exhibiting symptoms characteristic of that disease), and a negative control (a subject or a sample from a subject lacking the altered expression and clinical symptom of that disease).

"Differentially expressed" as applied to a gene, refers to the differential production of the mRNA transcribed from the gene or the protein product encoded by the gene. A differentially expressed gene may be overexpressed or underexpressed as compared to the expression level of a normal or control cell. In one aspect, it refers to a differential that is at least 1.5 times, or at least 2.5 times, or alternatively at least 5 times, or alternatively at least 10 times higher or lower than the expression level detected in a control sample. The term "differentially expressed" also refers to nucleotide sequences in a cell or tissue which are expressed where silent in a control cell or not expressed where expressed in a control cell.

As used herein, the term "modulate" means to vary the amount or intensity of an effect or outcome, e.g., to enhance, augment, diminish or reduce.

As used herein the term "ameliorate" is synonymous with "alleviate" and means to reduce or lighten. For example one may ameliorate the symptoms of sarcopenia by making them more bearable.

The present invention provides compounds which are in prodrug form. The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

SMN-Increasing Substances and Methods of Use

Sarcopenia, the age-related wasting and loss of strength, is an important neuromuscular problem of aging. It affects up to 50% of individuals by the 8th decade, and can lead to impaired mobility, loss of independence, and increased risk of mortality. The neuromuscular system is comprised of groups of muscle fibers innervated by a single alpha motor neuron, motor axon, and synapses, termed a motor unit. The normal development and maintenance of the motor unit is dependent on trophic interactions between muscle and motor neurons. Losses of muscle fiber, neuromuscular junction (NMJ), and motor neuron function have all been identified as potentially important factors in sarcopenia, but the influence of neural factors on loss of muscle function with aging has received less attention. Electromyographic measures in vivo enable longitudinal quantification of the functional output from a muscle group, determination of the number of functional motor neurons, and assessment of NMJ integrity.

Prominent functional loss from the motor neuron pool associated with changes in NMJ transmission have been found in aging mice. Importantly these findings are noted at earlier ages than features of muscle loss, which shows that motor neuron dysfunction and loss of connectivity are important and early consequences of aging. The reduced ability of motor neurons to repair and maintain effective synaptic connectivity is an important factor underlying the development of sarcopenia. High expression of SMN protein in motor neurons is required for NMJ formation and maintenance during both development and regeneration, and SMN expression in motor neurons can be insufficient for motor unit repair and maintenance during aging.

Increased SMN expression improves nerve regeneration in mice following sciatic nerve injury, and SMN overexpression can reduce aging-related motor unit losses and improve regeneration and maintenance at the NMJ.

In humans, SMN protein is encoded by two genes, SMN1 and SMN2 (Lefebvre et al. 1995). These genes differ by a single nucleotide which results in SMN2 exon7 being skipped in the majority of transcripts. The loss of the amino acids encoded by exon7 results in an SMN protein that does not oligomerize and gets rapidly degraded (Gennarelli et al. 1995; Lorson et al. 1998; Lorson et al. 2000; Burnett et al. 2009). In the autosomal recessive disorder, spinal muscular atrophy (SMA), SMN1 is lost or mutated and SMN2 is retained which results in insufficient SMN for motor neurons and developmental NMJ maturation (Lefebvre et al. 1995; Burghes et al. 2009; Kariya et al. 2008). In contrast, SMN reduction induced in adult mice (after NMJ maturation) results in no marked abnormalities, but if adult mice with reduced SMN undergo sciatic nerve injury there is a marked defect in repair (Kariya et al. 2014).

The individual being treated can be of any age. Specifically, the individual can be 30, 35, 40, 45, 50, 55, 60, 65, 70, 75, 80, 85, or 90 years old, or younger, older, or any amount in between. For example, the subject can be 35 years old or older. In one embodiment, the subject has not been diagnosed with spinal muscular atrophy (SMA). In another embodiment, the subject has been tested for SMA and it has been determined that the subject does not have SMA. SMA differs from sarcopenia and nerve injuries in multiple ways. Spinal muscular atrophy (SMA) is a neurological disorder characterized by loss of function of the anterior horn cells in the spinal cord that results from reduced levels of SMN protein as a result of homozygous mutation of the SMN1 gene.

Sarcopenia

Disclosed herein is a method of reducing sarcopenia in an individual, the method comprising: identifying an individual with sarcopenia, an individual with symptoms of sarcopenia, or an individual at risk for developing sarcopenia, wherein the subject is 35 years old or older; and administering to the individual a Survival Motor Neuron (SMN)-increasing substance, thereby reducing sarcopenia, sarcopenia symptoms, or the risk of sarcopenia in the individual.

Sarcopenia has been defined by the prior art as the appendicular skeletal muscle mass (kg/height$^2$ (m$^2$)) being less than two standard deviations below the mean of a young reference group (i.e., the t-score). A t-score is determined by measuring the axial skeletal muscle mass of a patient, typically by dxa (i.e., dual energy xray absorptiometry) or a similar and reproducible measure. The measurement of axial skeletal muscle mass can be used to follow the progress of the patient to determine if treatment is slowing, preventing, or reversing muscle mass decline.

Another type of patient that would benefit from the present invention is one that has suffered some loss of muscle mass, but who does not suffer from a condition that interferes with acts of daily living and/or prevents the subject from living an independent life (e.g., a patient who might soon need assisted living).

An individual can be diagnosed as having sarcopenia in a number of different ways. For example, sarcopenia can be measured using DXA (discussed above). DXA can be measured in combination with measuring gait speed (walking speed) (Muscaritoli et al. (2010) Clinical Nutrition 29(2): 154-9). DXA measures lean body mass in reference to a normal population. A diagnostic definition that measures muscle strength and physical performance can also be used. Examples of such definitions have been developed by those of skill in the art.

Treating sarcopenia includes slowing its progression, stopping its progression, and/or partially reversing it. An example of slowing the progression of sarcopenia is to change the length of time a patient would go from a t-score of −1.5 to −2 (e.g., if such a progression would normally take 5 years, then treating as used herein could slow this change to 10 years). Examples of partial reversal include reducing a t-score 0.1, 0.2, 0.3, 0.4, 0.5, 0.6, 0.7, 0.8, 0.9, 1.0 or more units (e.g., moving from a t-score of −2 to a t-score of −1.9, −1.8, −1.7, −1.6, −1.5, −1.4, −1.3, −1.2, −1.1, etc.). Treating sarcopenia can include inhibiting muscle catabolism and/or increasing muscle anabolism in a subject having or at risk of developing sarcopenia. It can also include improving the muscle:fat ratio in a subject having or at risk of developing sarcopenia.

Treating sarcopenia can be measured by improving the gait of a subject having or at risk of developing sarcopenia. For example, improving the gait of the subject can comprise increasing stride length, reducing stride frequency, reducing stance width variability or a combination thereof. It can also include improving muscle functionality of a subject having or at risk of developing sarcopenia. The improvement in muscle functionality can be demonstrated by a reduction in the time required to complete a timed get-up-and-go test. It can also be demonstrated by a reduction in the time required to complete a timed stand test.

Treating sarcopenia also includes delaying the onset of sarcopenia. For example, if a typical male age 50 would begin to see signs of sarcopenia by age 55, treatment according to the present invention could delay the onset 1, 2, 3, 4, 5, 6, 7, 8, 9, 10, or more years. Thus, treating sarcopenia would include treating patients who have not yet been diagnosed with sarcopenia, but who would be vulnerable or expected to be vulnerable to developing sarcopenia. Patients who are vulnerable or expected to be vulnerable also include (a) patients using glucocorticoid steroids, (b) patients with chronic infections, (c) patients with chronic inflammatory conditions (e.g., inflammatory bowel disease), and (d) patients with cancer.

Nerve Injury

Injuries to peripheral nerves can be caused by trauma, surgery, cancer and by congenital anomalies. Injuries to peripheral nerves can be also caused by radiation therapy, chemotherapy, metabolic/endocrine complications, inflammatory and autoimmune diseases, vitamin deficiencies, infectious diseases, toxic causes, accidental exposure to organic metals and heavy metals, drugs, amputations and disease or condition relating to a loss of motor or sensory nerve function. Nerve injury or lesion may include nerve transection, crush, compression, stretch, laceration (sharps or bone fragments), ischemia and blast. In addition, nerve injury or lesion may result from damage or disruption of the neuronal axons. Injuries to peripheral nerves can be also caused by radiation therapy, chemotherapy, metabolic/endocrine complications, inflammatory and autoimmune diseases, vitamin deficiencies, infectious diseases, toxic causes, accidental exposure to organic metals and heavy metals, drugs, amputations and disease or condition relating to a loss of motor or sensory nerve function. Nerve injury or lesion may include nerve transection, crush, compression, stretch, laceration (sharps or bone fragments), ischemia and blast. In addition, nerve injury or lesion may result from damage or disruption of the neuronal axons.

Disclosed herein are methods of treating an individual with nerve damage, the method comprising: identifying a subject with nerve damage; and administering to the subject a Survival Motor Neuron (SMN) protein-increasing substance, thereby reducing nerve damage and/or improving nerve function in the individual. The nerve damage can be caused by an injury, for example, such as a peripheral nerve injury. The nerve damage can also be caused by a mechanical traumatic brain, spinal cord or nerve tissue injury.

Increasing SMN Production

The SMN1 and SMN2 genes lie within the telomeric and centromeric halves, respectively, of a large, inverted duplication on chromosome 5q13. These genes share more than 99% nucleotide identity, and both are capable of encoding SMN (a 294-amino acid RNA-binding protein). Absence of SMN1 is partially compensated for by SMN2, which produces enough SMN protein to allow for relatively normal development in cell types other than motor neurons. However, SMN2 cannot fully compensate for loss of SMN1 because, although SMN2 is transcribed at a level comparable to that of SMN1, a large majority of SMN2 transcripts lack exon 7, resulting in production of a truncated, less stable SMN protein (Lefebvre et al., 1995; Kashima et al., 2007; Lefebvre et al. 1997; Coovert et al. 1997).

Disclosed herein are a variety of methods and compositions for increasing SMN production. While examples of such are given herein, it is noted that these examples are not intended to be limiting, and that the invention disclosed relates to any method or composition that increases SMN production, which is used to treat or prevent sarcopenia and/or nerve damage. For example, PCT Application WO2009146033, which is incorporated herein in its entirety, discloses various methods and compositions for increasing SMN production. However, the present disclosure is not limited to these examples.

Disclosed herein are SMN-increasing substances that increase the expression or activity of an SMN agonist (e.g. Pumilio homolog 1, eIF-4E, MAP1B, Rhol, type II BMP receptor, type II TGF-beta receptor, R-SMAD protein, FGF-2 or FGF-3 receptor, RAS, and MAP kinase) or another protein or gene product that regulates the expression or activity of the SMN agonist, such as a transcription factor or other protein that acts upstream of the SMN agonist in a particular signaling cascade. In one embodiment, the agent is a small molecule compound that directly or indirectly increases the expression and/or activity of the SMN agonist. These agents (SMN-increasing substances) can be used to treat or prevent sarcopenia and/or nerve damage, and are discussed in more detail herein (WO2009146033A3, incorporated by reference herein for its teaching concerning SMN increasing substances).

The present invention also encompasses a method of treating or preventing sarcopenia and/or nerve damage in a subject in need thereof comprising administering to the subject an SMN-increasing substance that decreases the expression or activity of a SMN antagonist. As used herein, a "SMN antagonist" is a gene or protein that negatively regulates SMN function. A SMN antagonist can also refer to a gene or protein that acts to interfere or compete for binding with SMN target proteins. SMN antagonists include, but are not limited to, Fmrl, Moesin, slik, SMAD6, and SMAD7. In some embodiments, an agent that decreases the expression or activity of a SMN antagonist is a small molecule compound that directly or indirectly decreases the expression and/or activity of the SMN antagonist. In other embodiments, an agent that decreases the expression or activity of a SMN antagonist is an antibody or fragment thereof that binds to the SMN antagonist and prevents its interaction with other proteins and/or inhibits its activity.

In certain embodiments, an agent that decreases the expression or activity of a SMN antagonist is an antisense nucleic acid targeted to a sequence of the SMN antagonist. Suitable antisense nucleic acids can comprise ribonucleotides or deoxyribonucleotides and preferably, have at least one chemical modification. Such modifications include without limitation locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). Other modifications of antisense nucleic acids to enhance stability and improve efficacy, such as those described in U.S. Pat. No. 6,838,283, which is herein incorporated by reference in its entirety, are known in the art and are suitable for use in the methods of the invention. Preferable antisense nucleic acids useful for inhibiting the expression and/or activity of a SMN antagonist are about 20 to about 200 nucleotides in length. Antisense nucleic acids can comprise a sequence that is at least partially complementary (e.g. at least about 75%, 80%, 85%, 90%, 95%, 96%, 97%, 98%, or 99% complementary) to a gene sequence for a SMN antagonist or portion thereof. In one embodiment, the antisense nucleic acid comprises a sequence that is 100% complementary to a gene sequence for a SMN antagonist or portion thereof. The antisense nucleic acid can target either a coding or non-coding region of the SMN antagonist gene. In some embodiments, the antisense nucleic acid targets an mRNA transcript from the SMN antagonist gene.

In other embodiments, an agent that decreases the expression or activity of a SMN antagonist is an inhibitory RNA molecule targeted to a sequence of the SMN antagonist. The inhibitory RNA molecule may be a double-stranded, small interfering RNA (siRNA) or a short hairpin RNA molecule (shRNA) comprising a stem-loop structure or a ribozyme. The double-stranded regions of the inhibitory RNA molecule may comprise a sequence that is at least partially identical and partially complementary, e.g. about 75%, 80%, 85%, 90%, 95%, 96%, 97%, 98%, or 99% identical and complementary, to a coding or non-coding region of a gene sequence for a SMN antagonist. In one embodiment, the double-stranded regions of the inhibitory RNA molecule may contain 100% identity and complementarity to the gene sequence for a SMN antagonist. In another embodiment, the inhibitory RNA molecule targets an mRNA transcript from the SMN antagonist gene.

The antisense nucleic acid or inhibitory RNA molecule targeted to a SMN antagonist can be encoded on an expression construct as described herein. In one embodiment, the antisense nucleic acid or inhibitory RNA molecule is under the control of a tissue-specific promoter. In a preferred embodiment, the tissue-specific promoter is a muscle-specific promoter. In another preferred embodiment, the tissue-specific promoter is a neuron-specific promoter.

SMN levels can be increased by preventing skipping of exon 7 of SMN2 (WO2001066129 A1, hereby incorporated by reference in its entirety for its disclosure of preventing skipping of exon 7 of SMN2). Accordingly, the present invention provides a substance which is capable of preventing the skipping (exclusion) of exon 7 of the SMN2 gene. Thus, the substance is suitable for the use as a therapeutic agent in treating or preventing sarcopenia and/or nerve damage.

The present invention also provides a process for changing the pre-mRNA processing relating to the SMN gene of a mammalian cell, which process comprises exposing the cell to a substance, which is capable of controlling the inclusion of exon 7 of the SMN2 gene, and thereby treating or preventing sarcopenia and/or nerve damage. The present invention also provides a mammalian host cell which is stably transfected with a DNA encoding a polypeptide which is capable of at least partially preventing the skipping (exclusion) of exon 7 of the SMN2 gene, thereby treating or preventing sarcopenia and/or nerve damage. The transfected mammalian host cell, which preferably originates from a human individual to be treated and/or from a cultured human cell or cell line, is useful in gene therapy to treat or prevent sarcopenia and/or nerve damage.

Also disclosed are methods of increasing SMN levels by altering SMN2 splicing (PCT Application WO2010120820 A1, hereby incorporated in its entirety for its disclosure concerning altered SMN2 splicing and antisense compounds targeted to SMN2). The present invention is directed to antisense compounds targeted to and hybridizable with a nucleic acid molecule encoding SMN2. Antisense compounds can be used to target intron 7 of SMN2, which compounds modulate splicing of SMN2 pre-mRNAs. In one embodiment, modulation of splicing results in an increase in exon 7 inclusion. In another embodiment, modulation of splicing results in a decrease in exon 7 inclusion. Disclosed herein are antisense compounds 16 to 30 nucleotides in length targeted to intron 7 of SMN2, wherein the compounds comprise 2'-O-methoxyethyl sugar modifications, for example. Therefore, disclosed are methods of increasing SMN production, and thereby treating or preventing sarcopenia and/or nerve damage by using 2'-O-methoxyethyl (2'MOE) chemistry. The antisense compounds can be targeted to cis splicing regulatory elements. Regulatory elements include exonic splicing enhancers, exonic splicing silencers, intronic splicing enhancers and intronic splicing silencers. Exonic and intronic splicing silencers are preferred targets.

Also provided are methods for modulating splicing of SMN2 mRNA in a cell, tissue or organ, thereby treating or preventing sarcopenia and/or nerve damage in a subject. In one embodiment, modulation of splicing is exon inclusion. In another embodiment, modulation of splicing is exon skipping. In one aspect, the compound is targeted to an intronic splicing silencer element. In another aspect, the compound is targeted to an exonic splicing silencer element. These are discussed in further detail below. Also disclosed is the use of an antisense oligonucleotide for the preparation of a medicament for modulating splicing of an SMN2 pre-mRNA. In one aspect, modulation of splicing results in an increase in exon 7 inclusion. Use of an antisense oligonucleotide provided herein for the treatment or prevention or sarcopenia and/or nerve damage is further provided.

Also disclosed herein is a method of increasing SMN production by blocking long noncoding RNAs. Small molecules that activate the SMN promoter also act on SMN1. The down-regulation of long noncoding RNA which regulate SMN level (in particular in neurons) activates both SMN1 and SMN2, and gives much higher SMN expression.

Also disclosed are methods for treating or preventing sarcopenia and/or nerve injury using the polycomb repressive complex 2 (PRC2)-interacting RNAs to increase or enhance production of SMN1 or SMN (WO02013173638 A1, hereby incorporated by reference in its entirety for its disclosure concerning long noncoding RNAs and SMN). Polycomb repressive complex 2 (PRC2) is a histone methyltransferase and a known epigenetic regulator involved in silencing of genomic regions through methylation of histone H3. Among other functions, PRC2 interacts with long noncoding RNAs (lncRNAs), such as RepA, Xist, and Tsix, to catalyze trimethylation of histone H3-lysine27. PRC2 contains four subunits, Eed, Suzl2, RbAp48, and Ezh2. Single stranded oligonucleotides that bind to PRC2-associated regions of RNAs (e.g., lncRNAs) which can arise from within a genomic region that encompasses or that is in functional proximity to the SMN1 or SMN2 gene can induce or enhance expression of SMN1 or SMN2. This upregulation can result from inhibition of PRC2 mediated repression of SMN1 or SMN2.

Disclosed herein are methods of increasing SMN2 production by administering aryl substituted thiazol-2-yl-piperidines or related compounds (PCT Application WO2011130515 A1, hereby incorporated by reference in its entirety for its disclosure concerning increasing SMN2 production using aryl substituted thiazol-2-yl-piperidines). For example, compounds and pharmaceutically acceptable salts of Formula I and Formula II are provided herein.

Formula I
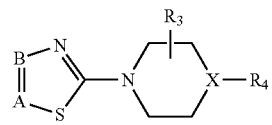

Formula II
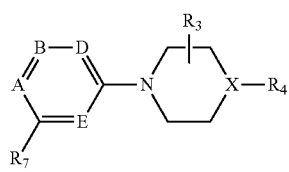

Compounds of Formula III, IV, and V are also provided herein.

Formula III
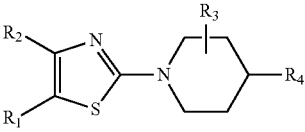

Formula IV
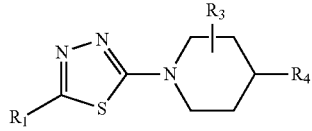

Formula V
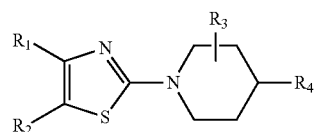

These compounds are subformulae of Formula I in which:

X is CH, A is CRi and B is CR2 (Formula III);

X is CH, A is CRi and B is N (Formula IV); and

X is CH, A is CR2 and B is CRi (Formula V).

The variables in Formula III, IV, and V may carry the definitions set forth for Formula I or any of the definitions set forth below.

Compounds of Formula VI, VII, VIII, IX, and X are also provided herein.

Formula VI
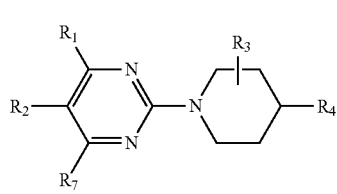

Formula VII
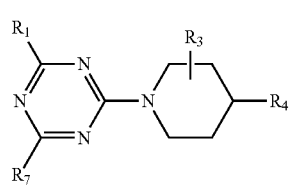

Formula VIII
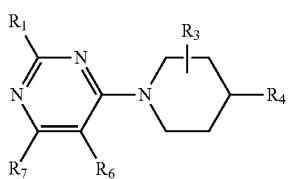

Formula IX
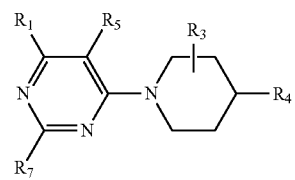

Formula X
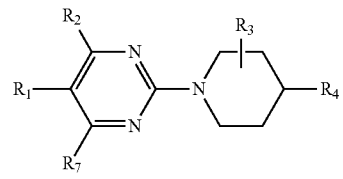

Compounds of subformulae VI to X are subformulae of Formula II in which: X is CH, A is $R_2$, B is Rh D is N, and E is N (Formula VI);

X is CH, A is N, B is Ri, D is N, and E is N (Formula VII);

X is CH, A is N, B is Ri, D is N, and E is CR6 (Formula VIII);

X is CH, A is N, B is Ri, D is CR5, and E is N (Formula IX); and X is CH, A is Ri, B is R2, D is N, and E is N (Formula X).

Also disclosed are method of increasing SMN2 production by administering ubiquitin carboxyl-terminal hydrolase L1 (UCHL1) regulators or related compounds. Disclosed herein is a method of treating or preventing sarcopenia and/or nerve damage comprising regulating the expression level of survival of motor neuron 1 (SMN1) comprising administering to a subject in need thereof a therapeutically effective amount of ubiquitin carboxyl-terminal hydrolase L1 (UCHL1) regulator and a pharmaceutically acceptable carrier. The protein expression level of SMN1 of the present invention is reduced by ubiquitin carboxyl-terminal hydrolase L1 (UCHL1) regulator, wherein the ubiquitin carboxyl-terminal hydrolase L1 (UCHL1) reduces the expression level of SMN1 by increasing the level of ubiquitinated SMN1.

Disclosed herein are tricyclo-DNA (tc-DNA) antisense nucleotides that are effective in facilitating exon skipping during pre-mRNA processing, in masking intronic silencer sequences and/or stem-loop sequences in pre-mRNA, and in targeting the RNase-mediated destruction of mRNA. Described herein are tc-DNA antisense nucleotides that may be used in methods for the treatment or prevention of sarcopenia and/or nerve damage by skipping mutated exons, such as masking an intronic silencing sequence and/or a terminal stem-loop sequence within an SMN2 gene to yield modified functional SMN2 protein, including an amino acid sequence encoded by exon 7, which is capable of at least partially complementing a non-functional SMN1 protein. (See U.S. Patent Application US20120149756, herein incorporated by reference in its entirety for its teaching concerning tricyclo-DNA).

SMN production can also be increased by binding the intronic inhibitory sequence element, named ISS-N1 (for "intronic splicing silencer"), located in the SMN2 gene (U.S. Pat. No. 8,586,559, hereby incorporated by reference in its entirety for disclosing ISS-N1 as it relates to SMN). The compositions and methods of the instant invention include oligonucleotide reagents (e.g., oligoribonucleotides) that effectively target the SMN2 ISS-N1 site in the SMN2 pre-mRNA, thereby modulating the splicing of SMN2 pre-mRNA to include exon 7 in the processed transcript. The ISS-N1 blocking agents of the invention cause elevated expression of SMN protein, thus compensating for the loss of SMN protein expression.

Also disclosed herein is the use of human SMN-like protein (HSLP), the polynucleotides encoding HSLP, and the use of these compositions and variants thereof for the treatment or prevention of sarcopenia and/or nerve injury (U.S. Pat. No. 6,130,064, hereby incorporated by reference in its entirety for its disclosure concerning HSLP).

SMN levels can be increased through gene therapy. Any gene delivery method known to those of skill in the art can be used with the methods disclosed herein. A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; artificial viral envelopes; recombinant yeast cells, metal particles; and bacteria or viruses, baculovirus, adenovirus and retrovirus, bacteriophage, cosmid, plasmid, fungal vectors and other recombination vehicles typically used in the art which have been described for expression in a variety of eukaryotic and prokaryotic hosts and may be used for gene therapy as well as for simple protein expression. Specifically, disclosed is the use of an adeno-associated virus, particularly AAV9.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. (Schlesinger and Dubensky (1999) Curr. Opin. Biotechnol. 5:434-439 and Ying et al. (1999) Nat. Med. 5(7):823-827). In aspects where gene transfer is mediated by a retroviral vector, a vector construct refers to the polynucleotide comprising the retroviral genome or part thereof and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, "retroviral vector" refers to a viral particle capable of introducing exogenous nucleic acid into a cell through a viral or viral-like entry mechanism.

In aspects where gene transfer is mediated by a DNA viral vector, such as an adenovirus (Ad) or adeno-associated virus (AAV), a vector construct refers to the polynucleotide comprising the viral genome or part thereof and a transgene. Wild-type AAV has high infectivity and specificity integrating into the host cell's genome.

Vectors that contain both a promoter and a cloning site into which a polynucleotide can be operatively linked are well known in the art. Such vectors are capable of transcribing RNA in vitro or in vivo and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, recombinant yeast cells and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragment(s) thereof which bind cell surface antigens, e.g., TCR, CD3 or CD4.

Preferably, a pharmaceutically effective amount of an agent for treating or preventing sarcopenia or nerve injury is administered to the subject (e.g. human subject). As used herein, the term "pharmaceutically effective amount" means an amount that improves one or more symptoms.

Formulation of an agent described herein for treatment purposes comprises combining pharmaceutically effective amounts of the agent of the invention with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosol, benzyl alcohol) and bulking substances (e.g., lactose, mannitol); incorporation of the material into particulate preparations of polymeric compounds such as polylactic acid, polyglycolic acid, etc. or into liposomes. Protein agents of the invention may be produced as fusion proteins to modulate or extend the half-life of the protein. Such fusion proteins may include human serum albumin, transferrin, other serum proteins, etc. Such compositions may influence the physical state, stability, rate of in vivo release, and rate of in vivo clearance of the present compounds. See, e.g., Remington's Pharmaceutical Sciences, 18th Ed. (1990, Mack Publishing Co., Easton, Pa. 18042) pages 1435-1712. The compositions may be prepared in liquid form, or may be in dried powder, such as lyophilized form. Implantable sustained release formulations are also contemplated. Preferably, pharmaceutical compositions will be prepared in a form appropriate for the intended application and be essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, can be used as delivery vehicles for the therapeutic agents described herein, especially for nucleic acid-based therapeutic agents (e.g. expression vectors, antisense nucleic acids, and inhibitory RNA molecules). Commercially available fat emulsions that are especially suitable for delivering the nucleic acid agents of the invention to tissues, such as skeletal muscle tissue, include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO 03/093449, which are herein incorporated by reference in their entireties.

Administration of the agents according to the methods of the present invention may be via any common route so long as the target tissue (e.g. skeletal muscle, motor neurons) is available via that route. This includes oral, nasal, or buccal. Alternatively, administration may be by intradermal, subcutaneous, intramuscular, intraperitoneal, intrathecal, intraventricular, intraparenchymal, intraarterial or intravenous injection, or by direct injection into skeletal muscle tissue or motor neurons. The therapeutic agents described herein would normally be administered as pharmaceutically acceptable compositions, as described herein. The agents may also be administered parenterally or intraperitoneally. By way of illustration, solutions of the therapeutic agents as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture, storage, and administration (depot delivery) and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the therapeutic agents in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof. Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intrathecal, intravenous, intramuscular, subcutaneous and intraperitoneal administration. Preferably, sterile aqueous media are employed as is known to those of skill in the art, particularly in light of the present disclosure. Some variation in dosage will necessarily occur depending on the stage of disease to be treated and individual characteristics of the subject to be treated {e.g. size, age, overall health, etc.). The person responsible for administration will, in any event, determine the appropriate dose for the individual subject. Moreover, for human administration, preparations should meet sterility, pyrogenicity, general safety and purity standards as required by FDA Office of Biologies standards.

Any SMN-increasing agents disclosed herein can be co-administered with another SMN-increasing agent. In other words, one, two, three, or more of SMN-increasing agents or methods of treatment can be administered simultaneously, or before or after each other. Also disclosed are methods comprising administering an SMN-increasing agent as well as another method or composition known for treating or preventing sarcopenia. For example, compositions known to treat or prevent sarcopenia include, but are not limited to, testosterone, estrogen, growth hormone, creatine, or beta-alanine.

The subject can also be advised concerning diet and exercise. For example, disclosed herein are methods of treating or preventing sarcopenia and/or nerve damage in an individual, comprising providing an SMN-increasing substance, as well as providing information regarding exercise and nutrition.

Also disclosed are methods comprising administering an SMN-increasing agent as well as another method or composition known for treating nerve injury. For example, compositions known to treat nerve injury include, but are not limited to, neuregulin, tegaserod, or follistatin. Also disclosed is inhibiting myostatin, or administering a TNF-α inhibitor.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Loss of Motor Unit Function During Aging and SMN Overexpression

Electromyographic Studies and Aging-Related Changes

Muscle wasting by ~2 years has been shown to occur in aging mice, and this loss of muscle mass appears to develop sometime after 15 months of age (Sayer et al. 2013; Shavlakadze et al. 2010). Prominent morphological alterations at the NMJ have also been identified in aged mice, but reports vary regarding the extent of histological loss of alpha motor neurons in aging mice. (Chai et al. 2011; Sayer et al. 2013; Jang et al. 2010). In 27 month old mice, in which overt motor neuron cell body loss was not identified, fiber type grouping consistent with loss of motor neurons (and compensatory reinnervation) was identified when compared with young adult mice (Chai et al. 2011). In various hind limb muscles of 2 year old mice, up to 20% of synapses may be fully denervated (not including partially denervated or morphologically altered synapses) (Chai et al. 2011; Valdez et al. 2010; Wang et al. 2005). Loss of muscle mass and strength are consequences of the functional loss of motor units and motor unit connectivity (with or without histological loss of the cell body of the motor neuron). This shows the value of a functional measure of the entire motor unit, rather than isolated histological analyses at the junction and motor neuron. Loss of motor neuron function can be central to sarcopenia, and aging-related weakness and muscle wasting emerge as the ability of the motor unit pool to compensate for these losses becomes insufficient. This can be related to insufficient numbers of functional motor neurons or intrinsic failure of individual motor neurons to maintain synaptic connections. Loss of motor unit function can occur much earlier than previously realized (presented later in FIG. 1), which have gone unnoticed due to the ability of the mouse to undergo significant compensation through collateral sprouting. Therefore many of the previously observed changes at the synapse and in muscle can reflect secondary changes of earlier degenerative events that occur during aging.

Figure 1C:
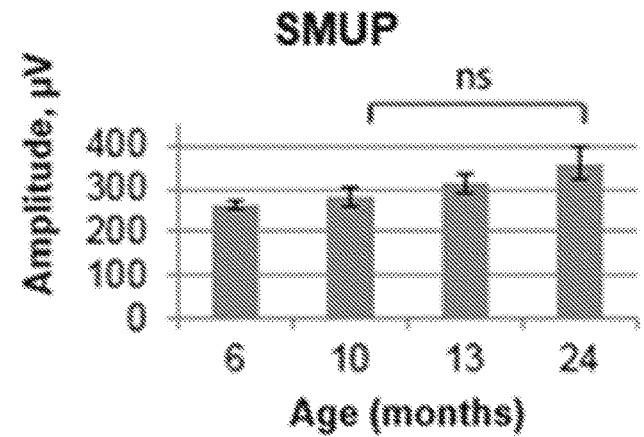
Figure 1D:
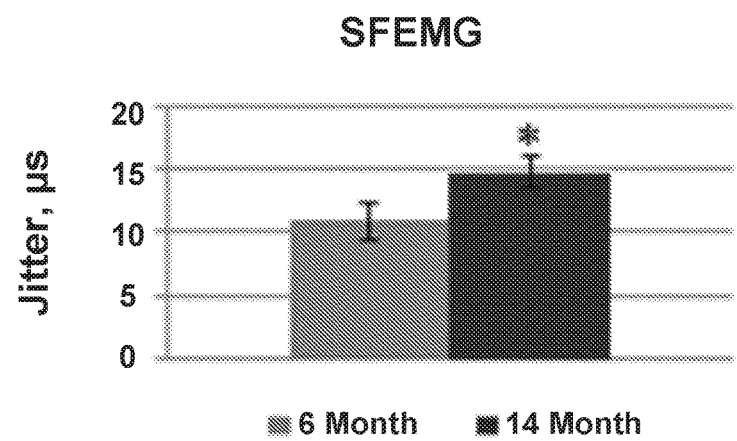

Electromyographic studies can be utilized to observe the aging-related changes that occur in a longitudinal fashion. Identification of the early events can help to understand the primary and secondary changes that occur with aging over time. Of particular importance is the fact that these measures are modified from similar measurements that can be obtained in clinical studies. Therefore the ability to readily translate findings from animal studies is significantly increased. Compound muscle action potential (CMAP) amplitude is an assay of the functional output of the motor unit pool, regardless of whether functional loss occurs at the muscle fiber, synapse, motor axon, or motor neuron level. Motor unit number estimation (MUNE) provides an estimation of the number of functional motor units/neurons/motor axons. CMAP responses following repetitive nerve stimulation (RNS) can be recorded to assess sufficiency of NMJ transmission. Single fiber electromyography is utilized to assess NMJ transmission at single synapses. SFEMG findings that signify reduced safety factor (jitter) or insufficient safety factor to reach threshold (blocking) are the most sensitive parameters of abnormal NMJ transmission in vivo (Stalberg et al. 1997; Juel 2012). These electromyographic studies are utilized to understand the function of the entire motor unit, which are then correlated with other force measures in vivo and histological measures. Electromyographic studies have been performed from cohorts of C57BL/6J male mice at 3, 6, 10, 14, and 24 months of age. Prominent functional loss from the motor neuron pool innervating the hind limb muscles have been shown in aging mice, and these findings begin to emerge at ~13 months (FIG. 1). By 24 months motor unit number estimation (MUNE) is significantly reduced by ~35% compared with 10 month old mice consistent with loss of motor neuron function (FIG. 1A). These findings with MUNE are consistent with recently published results of motor axon counts in aged mice showing 35% loss at the L1 ventral root (Valdez et al. 2010). Importantly, MUNE has advantages over anatomical counts due to the ability of MUNE to estimate the number of functional motor units/neurons, rather than presence or absence of motor neuron cell body or ventral root counts (i.e. histological loss). Single motor unit potential amplitude (or SMUP) is an assay of the output of a single motor unit or neuron. SMUP amplitude is increased by ~28% in 2 year old mice (FIG. 1B) consistent with compensatory reinnervation in response to denervation. Nevertheless, CMAP amplitude is not maintained in 24 month old mice and is reduced by ~25% compared with 10 month old mice (FIG. 1C). Therefore the reduced CMAP in the 24 month old animals identifies the inability of the remaining motor neurons to maintain a normal functional output from the muscle. NMJ transmission recordings utilizing axonal stimulation-SFEMG from the lateral gastrocnemius muscle demonstrate increased jitter in 14 month old mice 14.7±1.1 μs (n=22 synapses/single muscle fibers) compared with 6 month old mice is 10.8±1.4 μs (18 synapses/single muscle fibers) (p=0.04) (FIG. 1D). Repetitive nerve stimulation (RNS) demonstrate CMAP decrement (abnormal NMJ transmission) in 50% (n=6) of 24 month old mice compared with no mice (n=10) at 10 months (p=0.036) also supporting functional changes at the NMJ. Importantly changes of motor neuron failure and reinnervation are occurring in these mice (reduced MUNE and increase SMUP size noted above), therefore the NMJ defects noted can be secondary to failure at the motor neuron or ineffective formation and maintenance of the NMJ.

SMN2 Mouse Models

SMN protein is critical to motor neuron function and survival and low levels lead to motor neuron degeneration (Burghes et al. 2009; Arnold et al. 2013). If SMN reduction occurs after maturation of the NMJ, mice have no marked defects in early adulthood but during aging develop worsening NMJ defects and have impaired ability to reform effective synapses following nerve injuries (Kariya 2014). SMN can have an important role in aging and maintenance of the functional connectivity of the motor neuron at the synapse. SMA mouse models with the human SMN2 transgene and knockout of the mouse Smn gene (and therefore low levels of SMN protein) have been generated to investigate spinal muscular atrophy (Monami et al. 2000). Additionally, high copy SMN2 mice (both 8 copy and 16 copy) were generated to study the effects of high SMN levels (Monani et al. 2000) and have been maintained on a FVB background in the colony for over 15 years. Different breeding strategies can be utilized to generate mice with varying levels of SMN.

In humans, sarcopenia is linked to not only loss of function and independence of activities of daily living but also an increased risk of early mortality (Sayer et al. 2013; Landi et al. 2013; Batsis et al. 2014; Atkins et al. 2014). It was shown that mice harboring high copy numbers of the SMN2 transgene (on a FVB background) live longer than wild type FVBN mice. A median survival of 591 days and 760 days in male and female FVB mice, respectively, was previously shown (Yuan et al. 2009). Whereas mice in the colony with 16 copies of the SMN2 transgene (and homozygous null alleles for the mouse Smn gene) on a FVB background have a median survival of 900 days for males (n=12) and 945 days for females (n=6). This shows that SMN protein levels modulate the effects of aging.

Wild-type FVB mice are compared to mice with 8 copies of the SMN2 transgene and mice with 16 copies of the SMN2 transgene (both lacking a functional mouse Smn gene). Mice are analyzed longitudinally with non-invasive measures of motor unit function (electromyographic and force-described below). These longitudinal measures are compared with cohorts of aged mice for endpoint measures of SMN mRNA transcript levels (enriched motor neuron samples via laser capture microdissection) as well as pathological correlates at the ventral root, NMJ and muscle (described herein). In this manner, it is determined which degenerative changes are occurring and the timing and severity of these changes. Furthermore, responsiveness of these changes to high levels of SMN expression in transgenic animals are determined. This determines that SMN levels can modulate the effects of aging on the motor unit.

A. Mouse Groups
Wild-type FVB mice
8-copy SMN2 mice (homozygous null for mouse Smn) with wild-type levels of SMN from SMN2 transgene
16-copy SMN2 (homozygous null for mouse Smtn) with 2× wild-type levels of SMN from SMN2 transgene For each of these groups, 5 males/5 females are included for longitudinal electromyographic and force measures and 3 males/3 females are included at each endpoint assessment of histology and SMN levels.

B. Longitudinal Electromyographic Studies
CMAP (output of motor unit pool supplying a muscle) CMAP responses are recorded from the triceps surae muscles to assess total electromyographic output from the triceps surae muscles (Duque et al. 2014; Arnold et al. 2014).
MUNE (# of functional motor neurons innervating a muscle) MUNE of the sciatic nerve is utilized to estimate the number of functional motor units innervating the triceps surae muscles (Duque et al. 2014; Arnold et al. 2014).
Repetitive Nerve Stimulation (RNS) and single fiber EMG (SFEMG) (NMJ transmission)
Two methods are utilized to assess NMJ transmission. RNS is a clinical electromyographic measure that involves recording the CMAP response following a train of stimuli. When NMJ transmission is sufficient, CMAP amplitude remains stable, but if endplate potentials are of insufficient amplitude to reach threshold for muscle fiber action potential generation, CMAP amplitude decrements (Arnold 2014). Single fiber EMG (SFEMG) is extracellular recording technique that utilizes a combination of narrow filter settings and small electrode surface to allow recording of single muscle fiber action potentials following axonal stimulation. SFEMG is the most sensitive measure of disruption of NMJ transmission in vivo, and it can be performed in human studies and animal models (Gooch et al. 2001; Meekins et al. 2007).

C. Force Measurements In Vivo:
Assessment of plantar flexion force (twitch force, maximum tetanic force, and force-frequency curve) is performed utilizing a whole mouse testing system with a force transducer and nerve stimulation in vivo. Force measurements are obtained in vivo for the benefits of being a physiological comparison to the electromyographic recordings. Force measurements are compared with muscle size to determine how motor unit changes relate to muscle quality, a important factor in aged muscle in humans (Newman et al. 2003; Newman et al. 2006; Misic et al. 2007; Kennis et al. 2014; Goodpaster et al. 2006.)

Figure 2A:
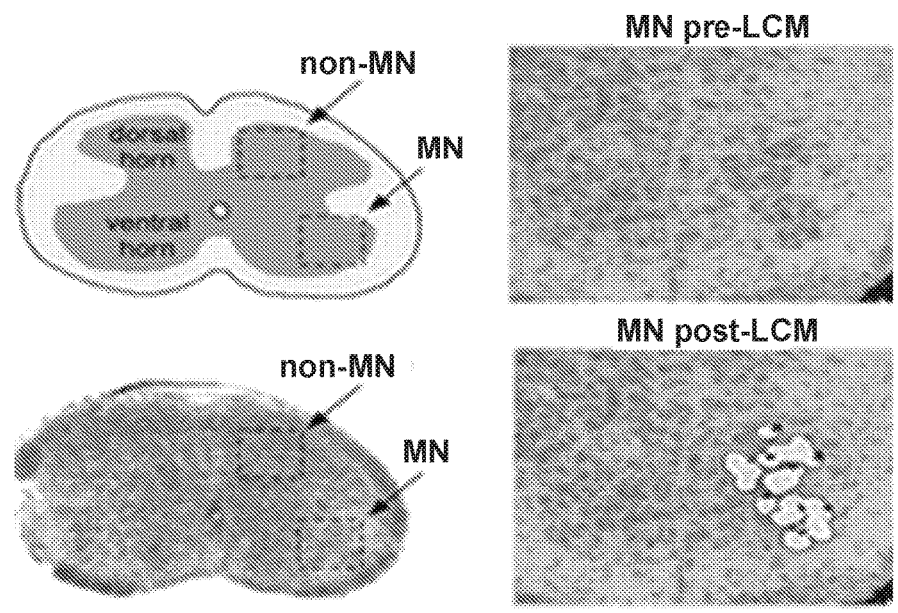
FIGS. 2A-2B show real-time PCR utilizing enriched motor neuron (M/IN) samples laser capture microdissection (LCM) (Ruggio et al. 2012).
Figure 2B:
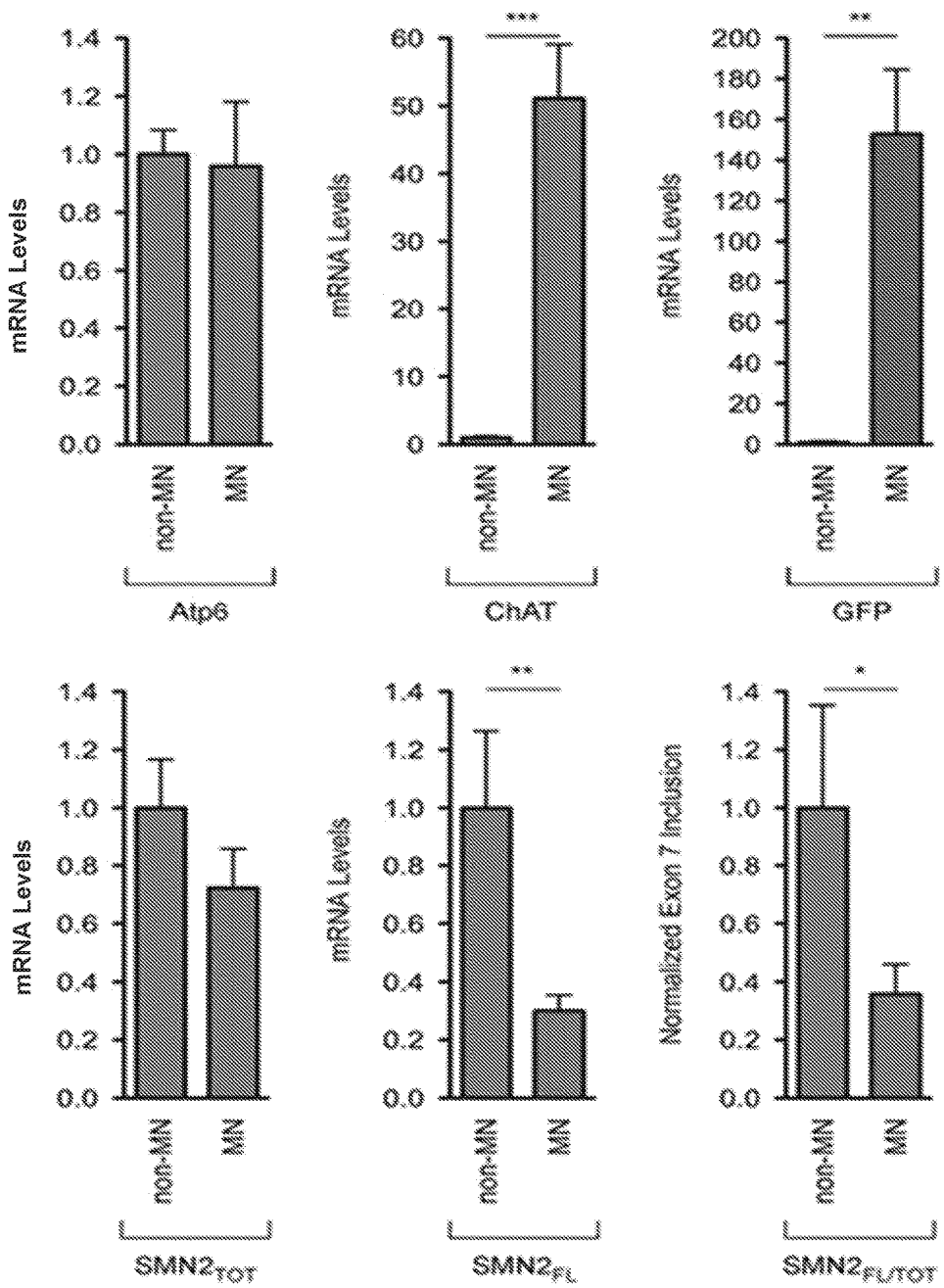

D. SMN Transcript Levels:
Enriched motor neuron samples are obtained via laser capture microdissection (FIG. 2) and assessed by droplet digital PCR (similar to our work in both mouse and the pig (Ruggiu et al. 2012; Duque et al. 2014) to measure SMN transcript levels in order to understand how these levels correspond to function of the motor unit and synaptic maintenance during aging.

E. Endpoint Morphological Measurements.
Muscle: Some histopathological features noted in muscle during aging recapitulate findings expected in denervation (e.g. type II fiber atrophy, grouped atrophy, angular atrophic fiber) as compared with features such as muscle fibers with central nuclei which corresponds with muscle fiber degeneration/regeneration (Carlson 1993). The histopathological response of muscle during aging is determined, and these findings are compared to the functional status of the motor unit. Tibialis anterior and gastrocnemius muscle characteristics of fiber size, type, nuclei location, and wet muscle weights are quantified.

L4 Ventral Root Counts: L4 ventral root motor axon counts are performed to determine the presence of motor axonal loss in the lower limb. L4 supplies both the tibialis anterior and gastrocnemius (Mohan et al. 2014), and L4 (and L3) spinal ventral roots consistently contribution to the sciatic nerve in the mouse, while L5 is less consistent (Rigaud 2008).

NMJ Innervation and Neurofilament Accumulation: Innervation status of NMJ's are quantified in the gastrocnemius and tibialis anterior. Due to its relevance to a SMN deficient state, splenius capitis, a posterior neck muscle that has shown particular susceptibility in SMN deficiency (Ling et al. 2012), is studied. Presynaptic neurofilament accumulation, also a prominent feature in SMA patients and mouse models (with low levels of SMN), is assessed with anti-neurofilament staining (Ling et al. 2012).

Linear mixed effects models are used to analyze electromyographic results (Arnold 2014). The rate of change for each genotype of mice is analyzed. The analysis of variance (ANOVA) with factors of age and genotype is conducted to pairwise compare the endpoints measures between genotypes within each age group (10, 18, 26 m) and between age groups for each genotype. The association of morphological and SMN transcript with electromyographic measures is evaluated by regression models. Including 10 mice (5 male/5 female) gives greater than 80% power to detect a 1.2-fold difference in the number of functional motor units, with coefficient of variation (CV)=20% (FIG. 1) at a=0.025 for 2 primary contrasts (8, 16 copies SMN2 vs WT). Increased power for the longitudinal study is due to the correlation of repeat measures in same animal. For the cohort of endpoints aging mice, n=6 (3 males/3 females) gives enough power to detect a 1.5 fold difference. Power calculations were performed using PASS 12 (NCSS, LLC;

Kaysville, Utah). Data analysis can be done by using SAS software (SAS, Inc., Cary, N.C.).

These studies provide insight to the components of the motor unit (muscle fiber, neuron, synapse) that are the earliest to show dysfunction, so that the compensatory changes of the motor unit following these early changes can be tracked. Functional, electrophysiological, and morphological measure determination allow a comprehensive look at the neuromuscular system with aging. Cross-sectional data shows that drop out of motor unit and synaptic function begins to occur between 10 and 13 months of age. Loss of motor neuron function can precede features of muscle wasting in aged mice. Loss of motor neuron function and associated secondary NMJ defects can occur simultaneously prior to losses in muscle fiber function due to enlargement of the single motor unit size. Alternatively, the earliest defects can occur at the synapse and loss of motor unit connectivity can be a later consequence. SMN overexpression in transgenic animals with 16 copies of SMN2 (and homozygous null mouse Smn alleles) can result in improved motor neuron and synaptic function during aging. Mice with 8 copies of SMN2 (and homozygous null mouse Snm alleles) and wild-type FVB mice can have similar features of aging-related motor unit degeneration over time (due to similar levels of SMN protein). Fully developed adult mice are assessed prior to any onset of electromyographic abnormalities (10 months) and these animals can be followed longitudinally until overt muscle atrophy is expected (24 months). This can capture mice pre-symptomatically and after onset of muscle loss. A gene therapy approach can also be used to transfer the SMN1 gene (Foust et al. 2010; Bevan et al. 2010) for testing SMN protein overexpression in other congenic strains. Additionally, telomerase deficient mice ($Terc^{-/-}$) can be used. Third generation $Terc^{-/-}$ mice have features of sarcopenia associated with reduced MUNE counts at 8 months are (173±44) compared with wild-type C57B6/J mice at 10 months age (341±29). These mice can be utilized to study the effects of aging on neuromuscular function.

Example 2: SMN Overexpression Improves Motor Axon Connectivity Following Injury

Figure 3A:
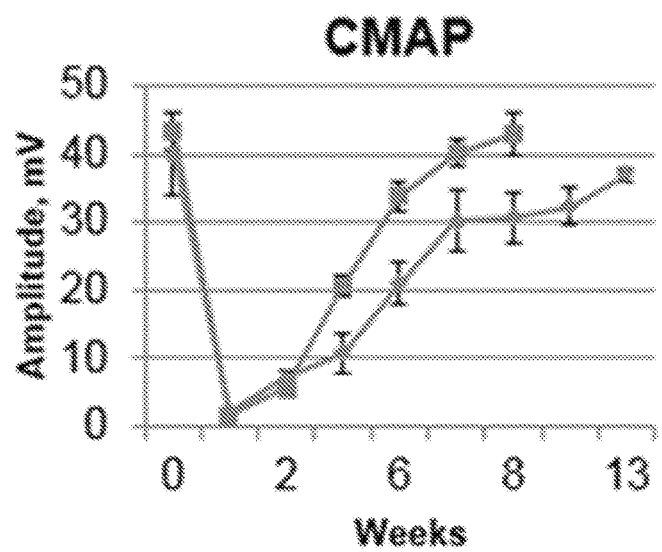
FIGS. 3A-3B show sciatic CMAP and MUNE recordings in wild type FVBN (WT, blue line) and transgenic FVBN mice with SMN protein overexpression (SMN overexpression, red line) following sciatic nerve crush at ~3 month old (time 0 weeks=measurement just prior to crush). A. CMAP amplitudes are increased in SMN overexpressing transgenic mice (n=6) compared with wild type mice (n=4) at 4, 6, 7, and 8 weeks (p<0.05). B. Similarly MUNE is increased in SMN overexpressing transgenic mice compared to wild type mice at 4, 6, 7, and 8 weeks post-crush. (P<0.05). (Data shown as mean±standard error).

Axonal sprouting and NMJ formation following nerve injury are less effective in aged mice, and aging motor neurons are unable develop as extensive innervation territory or output (Tanaka et al. 1991; Yuan et al 2012). Sciatic nerve crush studies resulted in an injury associated with complete recovery of CMAP response (functional output) by 80-100 days in wild type FVBN mice, but MUNE demonstrates incomplete motor unit repair with reduced numbers of functional motor neurons/units (FIGS. 3A and B). Therefore the nerve crush technique models a situation of complete recovery of functional output, but incomplete regeneration of innervating motor units. This system can be utilized to understand compensatory nerve repair activity and to test therapeutic targets to improve nerve repair activity.

Figure 3B:
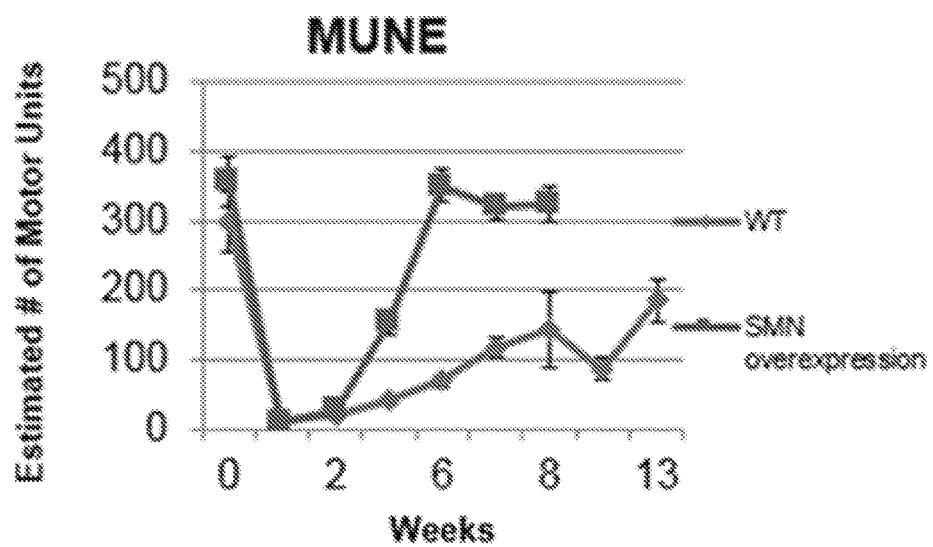

The data disclosed herein shows that transgenic mice with SMN overexpression have improved regenerative capacity following nerve injury compared with wild type mice. Importantly, the data show that increased SMN protein expression improves synaptic formation following nerve crush (FIG. 3). The early rate of repair activity in SMN overexpression mice (week 0 to week 2, which is dictated primarily by axonal sprouting) is similar to WT mice. In contrast, there is significant divergence between 2 weeks and 6 weeks post-crush, and this is consistent with the expected timing of NMJ formation/maturation. These findings are consistent with the prior work by Monani et al (analyzing NMJ formation histologically) in mice with wild type and deficient levels of SMN (Kariya et al. 2014). This repair activity can be critical during aging to maintain motor neuron function and NMJ connectivity. High levels of SMN protein can reduce degenerative susceptibility of the motor unit at the NMJ during injury and lessen the loss of regenerative capacity in aging mice.

Comparison is made between untreated young and old mice. Additionally, mice are treated with viral mediated gene transfer to assess the ability of SMN protein overexpression to improve axonal sprouting and synaptic formation following nerve crush injury in both young and aging animals. Therefore aging-related defects in repair activity (following nerve crush (Fahim et al. 1991; Landis et al. 2012)) can be corrected with SMN overexpression.

Testing Motor Neuron Repair Activity Following SMN Overexpression

Young Adult Mice (6 Months)
    8 males/8 females (AAV-SMN)
    8 males/8 females (AAV-empty vector)
    Aged Mice (24 Months)
    8 males/8 females (AAV-SMN)
    8 males/8 females (AAV-empty vector)

A. Double Sciatic Nerve Crush:
    Sciatic crush is performed in both young adult (at 6 months) and aged mice (at 24 months). The sciatic nerve are crushed utilizing a standardized technique (Bauder et al. 2012). Using hemostatic forceps the sciatic nerve is crushed for 15 seconds at 3 clicks of the hemostatic forceps. Then using the forceps the same crush site is crushed a second time for 15 seconds at 3 clicks force. Carbon can be applied to the second forceps to mark and therefore identify the lesion site for endpoint histology.

B. SMN Overexpression:
    There are two treatment cohorts in each age group: treatment with either scAAV-SMN or empty vector.

C. Longitudinal and Endpoint Analysis:
    The rate and extent of the recovery of motor neuron and synaptic function is assessed with longitudinal electromyographic and endpoint histopathology measures. For the entailed studies, 5 males and 5 females (10 mice) in each group are followed longitudinally for the entire 10 weeks post-crush and then undergo endpoint analysis. At four weeks crush, 3 males and 3 females (6 mice) in each group are euthanized for endpoint analysis.

10 and 6 mice/group are used for longitudinal and endpoints measures study, respectively. Longitudinal study is analyzed by mixed effect model and endpoints measures are analyzed by ANOVA. The rate of the change in electromyographic or endpoint measures are compared between groups (SMN vs empty vector) for aged or young mice, and between age group (aged vs young) for the mice with SMN overexpressed.

Regeneration of motor neuron and synaptic function can be impaired in placebo-treated aged animals (reduced number of functional motor neurons/units and impaired synaptic function). This loss of repair activity in aging mice can improved with increased SMN expression. In these treated animals, electromyographic measures demonstrate increased numbers of functioning motor units and improved synaptic transmission. Similarly morphological and force measures are improved. SMN expression increases during nerve regeneration (following nerve crush) (Kariya et al. 2014). SMN expression in untreated animals (following nerve crush and during nerve regeneration) can be diminished in aged compared to young mice.

Example 3: SMN Overexpression Improves Muscle Size and Function in Aged, Sarcopenic Mice Progressive changes of synaptic disruption and denervation are noted during the normal aging process in both humans and mice (Delbono 2003). Interestingly, these changes of denervation are absent in some neck muscles of the mouse (Li et al. 2011), but in leg muscles which are important for weight bearing and mobility (in mouse and humans) findings of denervation have consistently been noted (Chai et al. 2011; Valdez et al. 2010). Age-related alterations at the NMJ can originate from motor neuron loss, muscle fiber degeneration, and primary NMJ deficits. Synaptic signaling from denervated muscle fibers is critical during synaptic repair following muscle fiber injury (Doherty et al. 1993), but the origins of synaptic failure during aging have been unknown. Additionally, prior studies demonstrated a less robust response to partial denervation, which can be one important aspect of aging-related muscle weakness and wasting (Fahim et al. 1993; Jacob et al. 1990). These findings show the importance of denervation in the loss of function of aging individuals, and that denervation can be related to impaired maintenance of synaptic input to muscle fibers.

SMN expression is increased during both synaptic formation and maturation during development and during repair following an injury (Kariya et al. 2014). Interestingly, SMN expression is also increased during exercise (Biondi et al. 2008). A mouse model of SMA demonstrated increased SMN expression, preserved motor neuron counts, and prolonged survival following treadmill running exercise (Biondi et al. 2008). Thus, SMN protein appears to have significant importance with synaptic formation and can be regulated with increased synaptic activity.

Figure 4A:
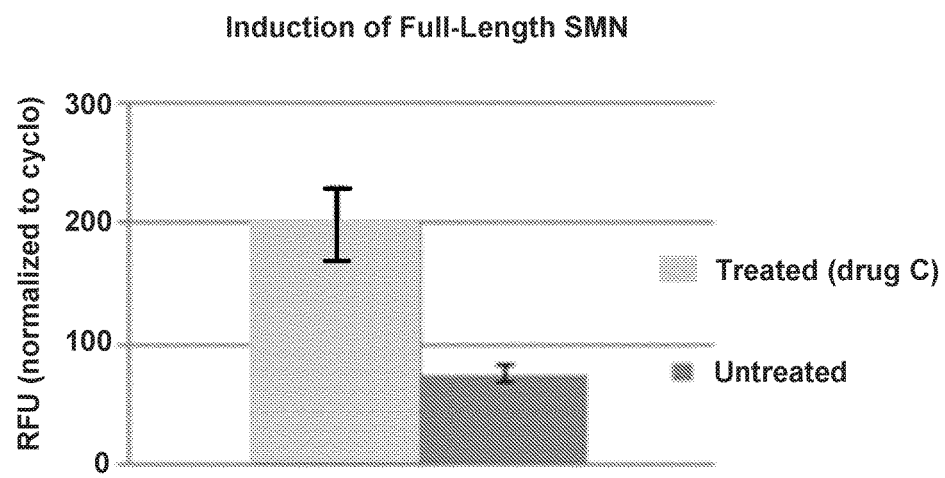
FIGS. 4A-4B show SMN induction. A. Induction of full-length SMN transcripts (from SMN2 transgene) after treatment with Drug C (digital PCR normalized to cyclophilin) (p<0.01). B. Structure of SMN-inducing Drug C.
Figure 4B:
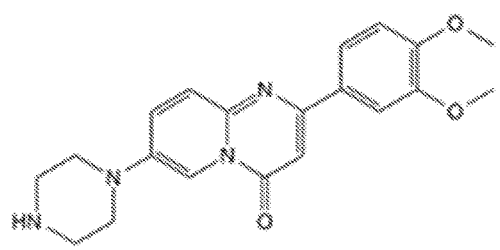
Figure 5:
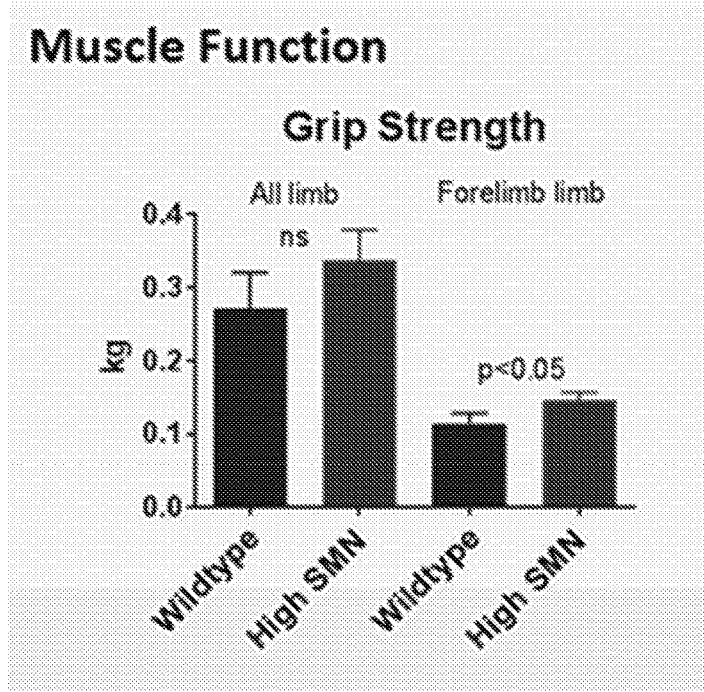
FIG. 5 shows aged mice with SMN overexpression demonstrate improved neuromuscular function compared with aged control mice.
Figure 5:
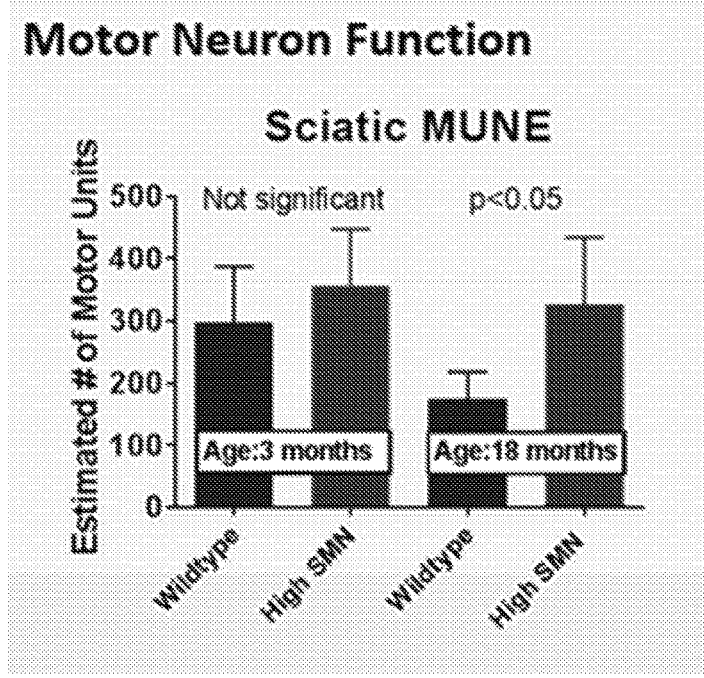
Figure 6:
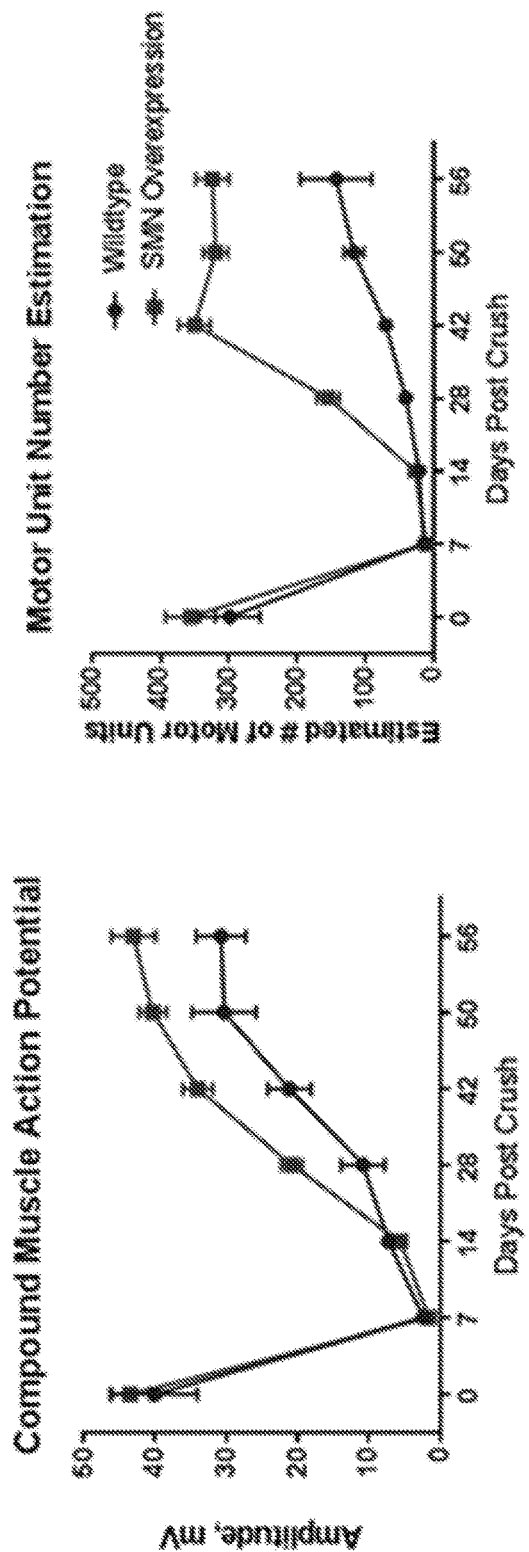
FIG. 6 shows mice with SMN overexpression demonstrate improved repair after nerve injury.

Drug compounds (such as Drug C, shown in FIG. 4) that efficiently stimulate full-length SMN from SMN2 (FIGS. 4A and B) are disclosed herein. Mice homozygous for a mouse Smn knockout allele that harbor 8 copies of a SMN2 transgene which are phenotypical normal and have SMN levels similar to wild-type mice (Monani et al. 2000). Thus these mice can be treated with SMN-inducing compounds that act on SMN2 to increase full-length SMN protein to test the effect of SMN overexpression on aging-related loss of muscle mass and function.

SMN protein can be used to correct muscle wasting in aging mice. Utilizing mice with the SMN2 transgene (8 copies) SMN protein expression (from the SMN2 transgene) is increased utilizing compounds that increase full-length SMN production from SMN2. Mice are monitored longitudinally with electromyographic recordings and force measurements in vivo and with endpoint histology. Muscle mass and function improvement is determined, and the mechanism of this improvement (i.e. improved synaptic transmission, increased number of functional motor neurons, or increased muscle size or function), can be assessed.

A. Smn-Overexpression:
16 mice (8 male/8 female) are treated with vehicle (placebo) and compared with 16 mice (8 male/8 female) treated with an SMN-inducing compound (such as Drug C shown in FIG. 4) to increase SMN protein expression. Treatment occurs after development of sarcopenia (24 months).

B. Longitudinal and Endpoint Analysis:
To measure the longitudinal effects on motor unit function, longitudinal electromyographic and force measures in vivo are performed (as described herein) at 18, 24, and 27 months. Endpoint morphological assessment is performed to assess full-length SMN transcript levels, NMJ innervation status, muscle fiber size, and ventral root counts at 27 months.

Treatment Groups at 24 Months
(After Onset of Muscle Loss)
  16 mice (8 male/8 female)
  (Drug C)
  16 mice (8 male/8 female)
  (Placebo/vehicle)

SMN overexpression, after onset of sarcopenia in 24 month-old mice can result in improved motor neuron connectivity and this can lead to improved muscle mass and function. SMN2 containing mice are used to assess small molecule SMN induction as a therapeutic strategy in sarcopenia. An alternative strategy for testing the effect of SMN overexpression in mice after onset of sarcopenia is gene transfer for induction of SMN overexpression rather than SMN2 containing mice and treatment with SMN-inducing compounds.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

1. Faulkner J A, Larkin L M, Claflin D R, Brooks S V Age-related changes in the structure and function of skeletal muscles. Clinical and experimental pharmacology & physiology. November 2007; 34(11):1091-1096.
2. Manini T M, Visser M, Won-Park S, et al. Knee extension strength cutpoints for maintaining mobility. Journal of the American Geriatrics Society. March 2007; 55(3):451-457.
3. Chai R J, Vukovic J, Dunlop S, Grounds M D, Shavlakadze T. Striking denervation of neuromuscular junctions without lumbar motoneuron loss in geriatric mouse muscle. PloS one. 2011; 6(12):e28090.
4. Valdez G, Tapia J C, Kang H, et al. Attenuation of age-related changes in mouse neuromuscular synapses by caloric restriction and exercise. Proceedings of the National Academy of Sciences of the United States of America. Aug. 17, 2010; 107(33):14863-14868.
5. Tomlinson B E, Irving D. The numbers of limb motor neurons in the human lumbosacral cord throughout life. Journal of the neurological sciences. November 1977; 34(2):213-219.
6. Oda K. Age changes of motor innervation and acetylcholine receptor distribution on human skeletal muscle fibres. Journal of the neurological sciences. November-December 1984; 66(2-3):327-338.
7. Kawamura Y, O'Brien P, Okazaki H, Dyck P J. Lumbar motoneurons of man II: the number and diameter distribution of large- and intermediate-diameter cytons in "motoneuron columns" of spinal cord of man. Journal of neuropathology and experimental neurology. September-October 1977; 36(5):861-870.
8. Arnold W D, Porensky P N, McGovern V L, et al. Electrophysiological Biomarkers in Spinal Muscular Atrophy: Preclinical Proof of Concept. Annals of clinical and translational neurology. Jan. 1, 2014; 1(1):34-44.
9. Fu A K Y, Cheung Z H, Ip N Y [beta]-catenin in reverse action. Nat Neurosci. 03/print 2008; 11(3):244-246.
10. Koliatsos V E, Clatterbuck R E, Winslow J W, Cayouette M H, Prices D L. Evidence that brain-derived neurotrophic factor is a trophic factor for motor neurons in vivo. Neuron. 3/1993; 10(3):359-367.
11. Ikeda K, Wong V, Holmlund T H, et al. Histometric effects of ciliary neurotrophic factor in wobbler mouse motor neuron disease. Annals of neurology. January 1995; 37(1):47-54.
12. Kablar B, Belliveau A C. Presence of neurotrophic factors in skeletal muscle correlates with survival of spinal cord motor neurons. Developmental dynamics: an official publication of the American Association of Anatomists. November 2005; 234(3):659-669.
13. Fahim M A. Morphological correlates of physiological responses in partially denervated mouse muscle during aging. International Journal of Developmental Neuroscience. 6/1993; 11(3):303-310.
14. Verdu E, Buti M, Navarro X. The effect of aging on efferent nerve fibers regeneration in mice. Brain Res. Oct. 23, 1995; 696(1-2):76-82.
15. Tanaka K, Webster H D. Myelinated fiber regeneration after crush injury is retarded in sciatic nerves of aging mice. The Journal of comparative neurology. Jun. 8, 1991; 308(2):180-187.
16. Yuan Q, Su H, Guo J, et al. Decreased c-Jun expression correlates with impaired spinal motoneuron regeneration in aged mice following sciatic nerve crush. Experimental gerontology. April 2012; 47(4):329-336.
17. Kariya S, Obis T, Garone C, et al. Requirement of enhanced Survival Motoneuron protein imposed during neuromuscular junction maturation. The Journal of clinical investigation. Feb. 3, 2014; 124(2):785-800.
18. Lefebvre S, Burglen L, Reboullet S, et al. Identification and characterization of a spinal muscular atrophy-determining gene. Cell. Jan. 13, 1995; 80(1):155-165.
19. Gennarelli M, Lucarelli M, Capon F, et al. Survival motor neuron gene transcript analysis in muscles from spinal muscular atrophy patients. Biochem Biophys Res Commun. Aug. 4, 1995; 213(1):342-348.
20. Lorson C L, Strasswimmer J, Yao J M, et al. SMN oligomerization defect correlates with spinal muscular atrophy severity. Nat Genet. May 1998; 19(1):63-66.
21. Lorson C L, Androphy E J. An exonic enhancer is required for inclusion of an essential exon in the SMA-determining gene SMN. Hum Mol Genet. Jan. 22, 2000; 9(2):259-265.
22. Burnett B G, Munoz E, Tandon A, Kwon D Y, Sumner C J, Fischbeck K H. Regulation of SMN protein stability. Molecular and cellular biology. March 2009; 29(5): 1107-1115.
23. Ruggiu M, McGovern V L, Lotti F, et al. A role for SMN exon 7 splicing in the selective vulnerability of motor neurons in spinal muscular atrophy. Molecular & Cellular Biology. 2012; 32(1):126-138.
24. Burghes A H, Beattie C E. Spinal muscular atrophy: why do low levels of survival motor neuron protein make motor neurons sick?. [Review] [171 refs]. Nature Reviews Neuroscience. 2009; 10(8):597-609.
25. Kariya S, Park G H, Maeno-Hikichi Y, et al. Reduced SMN protein impairs maturation of the neuromuscular junctions in mouse models of spinal muscular atrophy. Hum Mol Genet. Aug. 15, 2008; 17(16):2552-2569.
26. Monani U R, Sendtner M, Coovert D D, et al. The human centromeric survival motor neuron gene (SMN2) rescues embryonic lethality in Smn–/– mice and results in a mouse with spinal muscular atrophy. Human Molecular Genetics. Feb. 12, 2000 2000; 9(3):333-339.
27. Foust K D, Wang X, McGovern V L, et al. Rescue of the spinal muscular atrophy phenotype in a mouse model by early postnatal delivery of SMN. Nat Biotech. 2010; 28(3):271-274.
28. Arnold W D, Kassar D, Kissel J T. Spinal muscular atrophy: Diagnosis and management in a new therapeutic era. Muscle Nerve. Oct. 24, 2014.
29. Arnold W D, Burghes A H. Spinal muscular atrophy: The development and implementation of potential treatments. Annals of neurology. Aug. 12, 2013.
30. Kallman D A, Plato C C, Tobin J D. The role of muscle loss in the age-related decline of grip strength: cross-sectional and longitudinal perspectives. Journal of gerontology. May 1990; 45(3):M82-88.
31. Melton L J, 3rd, Khosla S, Crowson C S, O'Connor M K, O'Fallon W M, Riggs B L. Epidemiology of sarcopenia. Journal of the American Geriatrics Society. June 2000; 48(6):625-630.
32. Goodpaster B H, Park S W, Harris T B, et al. The loss of skeletal muscle strength, mass, and quality in older adults: The Health, Aging and Body Composition Study. J Gerentol Med Sci. 2006; 61:1059-1064.
33. Delmonico M J, Harris T B, Visser M, et al. Longitudinal study of muscle strength, quality, and adipose tissue infiltration. Am J Clin Nutr. December 2009; 90(6):1579-1585.
34. Newman A B, Haggerty C L, Goodpaster B, et al. Strength and muscle quality in a well-functioning cohort of older adults: the Health, Aging and Body Composition Study. Journal of the American Geriatrics Society. March 2003; 51(3):323-330.
35. Newman A B, Kupelian V, Visser M, et al. Strength, but not muscle mass, is associated with mortality in the health, aging and body composition study cohort. The journals of gerontology. Series A, Biological sciences and medical sciences. January 2006; 61(1):72-77.
36. Misic M M, Rosengren K S, Woods J A, Evans E M. Muscle quality, aerobic fitness and fat mass predict lower-extremity physical function in community-dwelling older adults. Gerontology. 2007; 53(5):260-266.
37. Li J G T, Arnold W D, Rosen G D, Zaworski P G, Rutkove S B. A comparison of three electrophysiological methods for the assessment of disease status in a mild spinal muscular atrophy mouse model. PLoS one. 2014; "In Press".
38. Duque S I, Arnold W D, Odermatt P, et al. A large animal model of Spinal Muscular Atrophy and correction of phenotype. Annals of neurology. Dec. 16, 2014.
39. Gooch C L, Mosier D R. Stimulated single fiber electromyography in the mouse: techniques and normative data. Muscle Nerve. July 2001; 24(7):941-945.
40. Meekins G D, Carter G T, Emery M J, Weiss M D. Axonal degeneration in the Trembler-j mouse demonstrated by stimulated single-fiber electromyography. Muscle Nerve. July 2007; 36(1):81-86.
41. Bevan A K, Hutchinson K R, Foust K D, et al. Early heart failure in the SMNDelta7 model of spinal muscular atrophy and correction by postnatal scAAV9-SMN delivery. Hum Mol Genet. Oct. 15, 2010; 19(20):3895-3905.
42. Bevan A K, Duque S, Foust K D, et al. Systemic gene delivery in large species for targeting spinal cord, brain, and peripheral tissues for pediatric disorders. Molecular therapy: the journal of the American Society of Gene Therapy. November 2011; 19(11):1971-1980.
43. Sayer A A, Robinson S M, Patel H P, Shavlakadze T, Cooper C, Grounds M D. New horizons in the pathogenesis, diagnosis and management of sarcopenia. Age and Ageing. Mar. 1, 2013, 2013; 42(2):145-150.
44. Shavlakadze T, McGeachie J, Grounds M D. Delayed but excellent myogenic stem cell response of regenerating geriatric skeletal muscles in mice. Biogerontology. June 2010; 11(3):363-376.
45. Jang Y C, Lustgarten M S, Liu Y, et al. Increased superoxide in vivo accelerates age-associated muscle atrophy through mitochondrial dysfunction and neuromuscular junction degeneration. FASEB journal: official publication of the Federation of American Societies for Experimental Biology. May 2010; 24(5):1376-1390.
46. Wang Z-M, Zheng Z, Messi M L, Delbono O. Extension and magnitude of denervation in skeletal muscle from ageing mice. The Journal of physiology. 2005; 565(3): 757-764.
47. Stalberg E, Trontelj J V The study of normal and abnormal neuromuscular transmission with single fibre electromyography. Journal of neuroscience methods. Jun. 27, 1997; 74(2):145-154.
48. Juel V C. Evaluation of neuromuscular junction disorders in the electromyography laboratory. Neurologic clinics. May 2012; 30(2):621-639.
49. Hsieh-Li HIMV, Chang J-G, Jong Y-J, et al. A mouse model for spinal muscular atrophy. Nat Genet. 2000; 24(1):66-70.
50. Landi F, Cruz-Jentoft A J, Liperoti R, et al. Sarcopenia and mortality risk in frail older persons aged 80 years and older: results from ilSIRENTE study. Age Ageing. March 2013; 42(2):203-209.
51. Batsis J A, Mackenzie T A, Barre L K, Lopez-Jimenez F, Bartels S J. Sarcopenia, sarcopenic obesity and mortality in older adults: results from the National Health and Nutrition Examination Survey III. European journal of clinical nutrition. September 2014; 68(9):1001-1007.
52. Atkins J L, Whincup P H, Morris R W, Lennon L T, Papacosta O, Wannamethee S G. Sarcopenic obesity and risk of cardiovascular disease and mortality: a population-based cohort study of older men. Journal of the American Geriatrics Society. February 2014; 62(2):253-260.
53. Yuan R, Tsaih S-W, Petkova S B, et al. Aging in inbred strains of mice: study design and interim report on median lifespans and circulating IGF1 levels. Aging Cell. 2009; 8(3):277-287.
54. Kennis E, Verschueren S, Van Roie E, Thomis M, Lefevre J, Delecluse C. Longitudinal impact of aging on muscle quality in middle-aged men. Age (Dordrecht, Netherlands). 2014; 36(4):9689.
55. Goodpaster B H, Park S W, Harris T B, et al. The loss of skeletal muscle strength, mass, and quality in older adults: the health, aging and body composition study. The journals of gerontology. Series A, Biological sciences and medical sciences. October 2006; 61(10): 1059-1064.
56. Carlson B M. The regeneration of skeletal muscle. A review. The American journal of anatomy. June 1973; 137(2): 119-149.
57. Mohan R, Tosolini A P, Morris R. Targeting the motor end plates in the mouse hindlimb gives access to a greater number of spinal cord motor neurons: An approach to maximize retrograde transport. Neuroscience. Aug. 22, 2014; 274(0):318-330.
58. Rigaud M, Gemes G, Barabas M E, et al. Species and strain differences in rodent sciatic nerve anatomy: implications for studies of neuropathic pain. Pain. May 2008; 136(1-2):188-201.
59. Ling K K Y, Gibbs R M, Feng Z, Ko C-P. Severe neuromuscular denervation of clinically relevant muscles in a mouse model of spinal muscular atrophy. Human Molecular Genetics. Jan. 1, 2012 2012; 21(1):185-195.
60. Ling K K, Gibbs R M, Feng Z, Ko C P. Severe neuromuscular denervation of clinically relevant muscles in a mouse model of spinal muscular atrophy. Hum Mol Genet. Jan. 1, 2012; 21(1):185-195.
61. Jacob J M, Robbins N. Age differences in morphology of reinnervation of partially denervated mouse muscle. J Neurosci. May 1990; 10(5):1530-1540.
62. Bauder A R, Ferguson T A. Reproducible mouse sciatic nerve crush and subsequent assessment of regeneration by whole mount muscle analysis. Journal of visualized experiments: JoVE. 2012(60).
63. Landis S C, Amara S G, Asadullah K, et al. A call for transparent reporting to optimize the predictive value of preclinical research. Nature. 10/11/print 2012; 490(7419): 187-191.
64. Delbono O. Neural control of aging skeletal muscle. Aging cell. February 2003; 2(1):21-29.
65. Li Y, Lee Yi, Thompson W J. Changes in Aging Mouse Neuromuscular Junctions Are Explained by Degeneration and Regeneration of Muscle Fiber Segments at the Synapse. The 50 Journal of Neuroscience. Oct. 19, 2011 2011; 31(42):14910-14919.
66. van Mier P, Lichtman J. Regenerating muscle fibers induce directional sprouting from nearby nerve terminals: studies in living mice. The Journal of Neuroscience. Sep. 1, 1994 1994; 14(9):5672-5686.
67. Biondi O, Grondard C, Lecolle S, et al. Exercise-induced activation of NMDA receptor promotes motor unit development and survival in a type 2 spinal muscular atrophy model mouse. J Neurosci. Jan. 23, 2008; 28(4):953-962.
68. Doherty T J, Vandervoort A A, Brown W F. Effects of ageing on the motor unit: a brief review. Canadian journal of applied physiology=Revue canadienne de physiologie appliquee. December 1993; 18(4):331-358.
69. Campbell M J, McComas A J, Petito F. Physiological changes in ageing muscles. Journal of Neurology, Neurosurgery & Psychiatry. Apr. 1, 1973 1973; 36(2):174-182.
70. Larsson L, Ansved T. Effects of ageing on the motor unit. Progress in neurobiology. April 1995; 45(5):397-458.
71. Mittal K R, Logmani F H. Age-related reduction in 8th cervical ventral nerve root myelinated fiber diameters and numbers in man. Journal of gerontology. January 1987; 42(1):8-10.
72. Aagaard P, Suetta C, Caserotti P, Magnusson S P, Kjaer M. Role of the nervous system in sarcopenia and muscle atrophy with aging: strength training as a countermeasure. Scandinavian journal of medicine & science in sports. February 2010; 20(1):49-64.
73. Sugarman E A, Nagan N, Zhu H, et al. Pan-ethnic carrier screening and prenatal diagnosis for spinal muscular atrophy: clinical laboratory analysis of >72,400 specimens. European journal of human genetics: EJHG. January 2012; 20(1):27-32.
74. McAndrew P E, Parsons D W, Simard L R, et al. Identification of proximal spinal muscular atrophy carriers and patients by analysis of SMNT and SMNC gene copy number. American journal of human genetics. June 1997; 60(6): 1411-1422.

75. Naryshkin N A, Weetall M, Dakka A, et al. SMN2 splicing modifiers improve motor function and longevity in mice with spinal muscular atrophy. Science (New York, N.Y.). Aug. 8, 2014 2014; 345(6197):688-693.

What is claimed is:

1. A method of reducing sarcopenia in an individual, the method comprising:
   a. identifying an individual with sarcopenia, an individual with symptoms of sarcopenia, or an individual at risk for developing sarcopenia, wherein the subject is 35 years old or older; and
   b. administering to the individual a Survival Motor Neuron (SMN)—increasing substance, thereby reducing sarcopenia, sarcopenia symptoms, or the risk of sarcopenia in the individual.

2. The method of claim 1, wherein SMN levels are increased through gene therapy.

3. The method of claim 1, wherein production of SMN from SMN2 is increased in the subject.

4. The method of claim 3, wherein SMN2 production is increased by administering aryl substituted thiazol-2-yl-piperidines or related compounds.

5. The method of claim 1, wherein SMN levels are increased through altered SMN2 splicing, preventing skipping of exon 7 of SMN2, blocking long noncoding RNAs, or administering ubiquitin carboxyl-terminal hydrolase L1 (UCHL1) regulators or related compounds.

6. The method of claim 1, wherein SMN production is increased through antisense oligonucleotides, blocking negative regulators of splicing, or binding ISSN1.

7. The method of claim 6, wherein the antisense oligonucleotide is a morpholino.

8. The method of claim 6, wherein SMN production is increased by using 2'-O-methoxyethyl (2'MOE) chemistry, tricyclo-DNA chemistry, locked nucleic acids, siRNA, shRNA, or activating an SMN promoter.

9. The method of claim 6, wherein the antisense oligonucleotide binds to SMN1 or SMN2.

10. The method of claim 1, wherein human SMN-like protein (HSLP) is increased in the subject.

11. The method of claim 1, wherein the subject has not been diagnosed with spinal muscular atrophy (SMA).

12. The method of claim 1, wherein the subject has been diagnosed with age-related muscle wasting.

13. The method of claim 1 wherein the method further comprises co-administering an additional composition for treating or preventing sarcopenia.

14. The method of claim 13, wherein the additional composition is testosterone, estrogen, creatine, beta-alanine, or growth hormone.

15. The method of claim 1, further comprising the step of counseling the subject regarding exercise and nutrition.

16. The method of claim 1, wherein the subject has an appendicular skeletal muscle mass t-score selected from among (a)<−3, (b)<−2.5, (c)<−2, (d)<−1.5, (e)<−1.0, and (f)<−0.5.

17. The method of claim 16, wherein the subject's appendicular skeletal muscle mass t-score is increased after at least 45 days of treatment, or is increased at least 90 days of treatment, or is increased after at least 180 days of treatment or is increased after at least one year of treatment.

18. The method of claim 17, wherein the appendicular skeletal muscle mass t-score is increased by at least 0.5 after treatment.

19. The method of claim 1, further comprising step c): measuring inhibition of muscle catabolism and/or increased muscle anabolism in the individual.

20. The method of claim 1, further comprising step c): measuring improvement in the muscle:fat ratio in the individual.

21. The method of claim 1, further comprising step c): measuring improvement in gait of the individual.

22. The method of claim 21, wherein improving the gait of the subject comprises increasing stride length, reducing stride frequency, reducing stance width variability or a combination thereof.

23. The method of claim 1, further comprising step c): measuring the prevention, treatment, mitigation, or amelioration of the onset, advancement, severity and/or symptoms of frailty in the individual.

24. The method of claim 1, further comprising step c): measuring an improvement in muscle functionality in the individual.

25. The method of claim 24, wherein the improvement in muscle functionality is demonstrated by a reduction in the time required to complete a timed get-up-and-go test.

26. The method of claim 24, wherein the improvement in muscle functionality is demonstrated by a reduction in the time required to complete a timed stand test.

* * * * *